US010391144B2

(12) United States Patent
Shah et al.

(10) Patent No.: US 10,391,144 B2
(45) Date of Patent: Aug. 27, 2019

(54) ATHEROSCLEROSIS INHIBITION VIA MODULATION OF MONOCYTE-MACROPHAGE PHENOTYPE USING APO A-I MILANO GENE TRANSFER

(71) Applicant: Cedars-Sinai Medical Center, Los Angeles, CA (US)

(72) Inventors: Prediman K. Shah, Los Angeles, CA (US); Behrooz Sharifi, Woodland Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 16/114,635

(22) Filed: Aug. 28, 2018

(65) Prior Publication Data
US 2018/0360911 A1 Dec. 20, 2018

Related U.S. Application Data

(62) Division of application No. 13/816,381, filed as application No. PCT/US2011/047940 on Aug. 16, 2011, now abandoned.

(60) Provisional application No. 61/410,806, filed on Nov. 5, 2010, provisional application No. 61/374,900, filed on Aug. 18, 2010.

(51) Int. Cl.
 A61K 48/00 (2006.01)
 A61K 38/17 (2006.01)
 C07K 14/775 (2006.01)
 C12Q 1/686 (2018.01)

(52) U.S. Cl.
 CPC .......... *A61K 38/1709* (2013.01); *A61K 48/00* (2013.01); *A61K 48/005* (2013.01); *C07K 14/775* (2013.01); *C12Q 1/686* (2013.01); *C12N 2799/025* (2013.01)

(58) Field of Classification Search
 None
 See application file for complete search history.

(56) References Cited

U.S. PATENT DOCUMENTS

| 7,527,795 | B2 | 5/2009 | Nilsson et al. |
| 7,528,225 | B2 | 5/2009 | Nilsson et al. |
| 7,537,758 | B2 | 5/2009 | Nilsson et al. |
| 7,544,360 | B2 | 6/2009 | Nilsson et al. |
| 7,556,811 | B2 | 7/2009 | Nilsson et al. |
| 7,691,965 | B2 | 4/2010 | Bielicki et al. |
| 7,704,499 | B2 | 4/2010 | Nilsson et al. |
| 7,785,589 | B2 | 8/2010 | Nilsson et al. |
| 8,025,876 | B2 | 9/2011 | Nilsson et al. |
| 8,029,786 | B2 | 10/2011 | Nilsson et al. |
| 8,034,336 | B2 | 10/2011 | Nilsson et al. |
| 8,119,590 | B2 | 2/2012 | Bisgaier et al. |
| RE43,581 | E | 8/2012 | Nilsson et al. |
| 8,926,958 | B2 * | 1/2015 | Shah ............ A61K 48/00 424/93.2 |
| 2003/0105003 | A1 | 6/2003 | Nilsson et al. |
| 2003/0109442 | A1 | 6/2003 | Bisgaier et al. |
| 2007/0098725 | A1 | 5/2007 | Nilsson et al. |
| 2007/0202081 | A1 | 8/2007 | Shah et al. |
| 2008/0234192 | A1 | 9/2008 | Heinecke et al. |
| 2008/0268029 | A1 | 10/2008 | Nilsson et al. |
| 2008/0274170 | A1 | 11/2008 | Nilsson et al. |
| 2008/0317837 | A1 | 12/2008 | Nilsson et al. |
| 2009/0117137 | A1 | 5/2009 | Nilsson et al. |
| 2009/0117178 | A1 | 5/2009 | Nilsson et al. |
| 2009/0202523 | A1 | 8/2009 | Nilsson et al. |
| 2009/0202555 | A1 | 8/2009 | Nilsson et al. |
| 2009/0226454 | A1 | 9/2009 | Nilsson et al. |
| 2009/0226475 | A1 | 9/2009 | Nilsson et al. |
| 2009/0280126 | A1 | 11/2009 | Nilsson et al. |
| 2010/0004430 | A1 | 1/2010 | Nilsson et al. |
| 2010/0183706 | A1 | 7/2010 | Nilsson et al. |

(Continued)

FOREIGN PATENT DOCUMENTS

| WO | 9312143 A1 | 6/1993 |
| WO | 2002080954 A1 | 10/2002 |

(Continued)

OTHER PUBLICATIONS

PCT/US11/47940 International Search Report dated Apr. 4, 2012.
Galinka et al. Immune and Inflammatory Mechanisms of Atherosclerosis. Annu. Rev. Immunol (2009). 27:165-197.
Khallou-Laschet et al. Macrophage Plasticity in Experimental Atherosclerosis. PloS One (2010). 5(1):1-10.
Mosser et al. Exploring the full spectrum of macrophage activation. Nat Rev. Immunol. (2008). 8(12): 958-969.
Shah et al. Effects of Recominant Apolipoprotein A-1 (Milano) on Aortic Atherosclerosis in Apolipoprotein E-Deficient Mice. Circulation (1998). 97:780-785.
Shah et al. High-dose recombinant apolipoprotein A-I(milano) mobilizes tissue cholesterol and rapidly reduces plaque lipid and macrophage content in apolipoprotein e-deficient mice. Potential implications for acute plaque stabilization. Circulation (2001). 103:3047-3050.

(Continued)

*Primary Examiner* — Michael D Burkhart

(74) *Attorney, Agent, or Firm* — Nixon Peabody LLP; Linda B. Huber; Suwei Zhu

(57) ABSTRACT

Embodiments of the present invention describe a method of changing the phenotype of monocytes and macrophages from a proinflammatory M1 phenotype to an anti-inflammatory M2 phenotype. The method can comprises providing a composition comprising a recombinant adeno-associated virus (rAAV) vector comprising an exogenous gene encoding ApoA-I Milano or a fragment thereof, and administering the composition to a mammal in need thereof to change the phenotype of monocytes or macrophages from a proinflammatory M1 phenotype to an anti-inflammatory M2 phenotype. By changing the phenotype of monocytes or macrophages from a proinflammatory M1 phenotype to an anti-inflammatory M2 phenotype, atherosclerosis can be treated. The present invention also describes a method of monitoring macrophage phenotypic switching and a method of assessing the efficacy of the treatment of atherosclerosis.

5 Claims, 17 Drawing Sheets

Specification includes a Sequence Listing.

(56) References Cited

U.S. PATENT DOCUMENTS

| | | | |
|---|---|---|---|
| 2012/0070899 | A1 | 3/2012 | Sharifi et al. |
| 2013/0115275 | A1 | 5/2013 | Nilsson et al. |
| 2013/0115276 | A1 | 5/2013 | Nilsson et al. |
| 2013/0115277 | A1 | 5/2013 | Nilsson et al. |
| 2013/0115278 | A1 | 5/2013 | Nilsson et al. |

FOREIGN PATENT DOCUMENTS

| | | |
|---|---|---|
| WO | 20030026492 A2 | 4/2003 |
| WO | 2005097206 A2 | 10/2005 |
| WO | 2010141706 A1 | 12/2010 |

OTHER PUBLICATIONS

Vaziri et al. In vitro stimuation of HDL anti-inflammatory activity and inhibition of LDL pro-inflammatory activity in the plasma of patients with end-stage renal disease by an apoA-1 mimetic peptide. Kidney International (2009). 76:437-444.

Wang et al. Bone Marrow Transplantation Shows Superior Atheroprotective Effects of Gene Therapy with Apolipoprotein A-1 Milano Compared with Wild-Type Apolipoprotein A-1 Hyperlipidemic Mice. J Am Coll Cardiol. (2006). 48(7): 1459-1468.

Ameli et al. Recombinant apolipoprotein A-I Milano reduces intimal thickening after balloon injury in hypercholesterolemic rabbits. Circulation (1994). 90(4):1935-1941.

Kanter et al., Do Glucose and Lipids Exert Independent Effects on Atherosclerotic Lesion Initiation or Progression to Advanced Plaques?, 2007, Circulation Research, vol. 100, pp. 769-781.

Kanter et al. Diabetes Promotes and Inflammatory Macrophase Phenotype and Atherosclerosis through acyl-CoA Synthetase 1, 2012, PNAS, pp. E715-E724.

Linton et al., Macrophages, Inflammation, and Atherosclerosis, 2003, Int. J. Obesity and Related Metabolic Disorders, 27 Suppl. 3, pp. S35-S40.

Lebherz et al., Gene Transfer of Wild-Type apoA-I and apoA-I Milano Reduce Atherosclerosis to a Similar Extent, 2007, Cardiovascular Diabetology, vol. 6(15), 8 Pages.

Kazunori Shimada, Immune System and Atherosclerotic Disease Heterogeneity of Leukocyte Subsets Participating in the Pathogenesis of Atherosclerosis, 2009, Cir. J., vol. 73, pp. 994-1001.

Zeyda et al., Adipose Tissue Macrophages, 2007, Immunology Letters, vol. 112, pp. 61-67.

\* cited by examiner

ATHEROSCLEROSIS INHIBITION VIA MODULATION OF MONOCYTE-MACROPHAGE PHENOTYPE USING APO A-I MILANO GENE TRANSFER

CROSS-REFERENCE TO RELATED APPLICATIONS

This application is a divisional of U.S. patent application Ser. No. 13/816,381 filed Feb. 11, 2013, which is a National Phase of International Application No. PCT/US2011/047940, filed Aug. 16, 2011, which designated the U.S. and that International Application was published under PCT Article 21(2) in English. This application also includes a claim of priority under 35 U.S.C. § 119(e) to U.S. provisional patent application No. 61/374,900, filed Aug. 18, 2010 and U.S. provisional patent application No. 61/410,806 filed Nov. 5, 2010.

FIELD OF INVENTION

This invention relates to the treatment of vascular diseases, including atherosclerosis; and to monitoring the treatment of vascular diseases, including monitoring surface markers on macrophages.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Atherosclerosis is just one of several types of arteriosclerosis, which is characterized by thickening and hardening of artery walls (e.g., coronary arteries, carotid arteries, aorta, and ileofemoral arteries). Over time, this material thickens, hardens and may eventually block or severely narrow the arteries. More than 61 million Americans suffer from some form of cardiovascular disease, including high blood pressure, coronary heart disease, stroke, congestive heart failure, and other conditions. More than 2,600 Americans die every day because of cardiovascular diseases. Thus, there is a need in the art for additional strategies for the treatment of atherosclerosis and the array of related diseases and physiological conditions, as well as methods to assess the phenotypic switching of macrophages and methods to monitor the efficacy of atherosclerosis treatment. While the inventors have observed potent anti-atherogenic effects of Apo A-I Milano gene transfer using retrovirally transduced bone marrow in Apo E−/−Apo A-1−/−double knockout mice, further studies to elucidate the mechanism of action are useful to provide additional therapeutic options for patients.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method, comprising: providing a composition comprising a recombinant adeno-associated virus (rAAV) vector comprising an exogenous gene encoding ApoA-I Milano, or fragment thereof; and administering the composition to a mammal in need of changing the phenotype of a monocyte or macrophage from a proinflammatory M1 phenotype to an anti-inflammatory M2 phenotype to change the phenotype of the monocyte or macrophage from the proinflammatory M1 phenotype to the anti-inflammatory M2 phenotype.

In various embodiments, the method can further comprise monitoring monocyte or macrophage phenotypic switching in the mammal. In various embodiments, the method can further comprise assessing the efficacy of a treatment for atherosclerosis in the mammal.

In various embodiments, the rAAV vector can be a rAAV8 vector comprising an exogenous gene encoding ApoA-I Milano or a fragment thereof. In certain embodiments, the rAAV8 can be produced by co-transfecting a host cell with a first plasmid and a second plasmid, wherein the first plasmid genome for the rAAV8 is derived from AAV serotype 2 and the second plasmid is derived from AAV serotypes 2 and 8 (Rep2Cap8).

In various embodiments, the rAAV vector can be a rAAV2 vector comprising an exogenous gene encoding ApoA-I Milano or a fragment thereof. In certain embodiments, the rAAV2 can be produced by co-transfecting a host cell with a first plasmid and a second plasmid, wherein the first plasmid genome for the rAAV2 is derived from AAV serotype 2 and the second plasmid is derived from AAV serotype 2 (Rep2Cap2).

In various embodiments, the monocyte or macrophage can be a circulating monocyte or macrophage. In various embodiments, the monocyte or macrophage can be a peritoneal monocyte or macrophage.

In various embodiments, changing the phenotype of the monocyte or macrophage from the proinflammatory M1 phenotype to the anti-inflammatory M2 phenotype can inhibit or treat atherosclerosis. In various embodiments, changing the phenotype of the monocyte or macrophage from the proinflammatory M1 phenotype to the anti-inflammatory M2 phenotype can reduce atherosclerosis. In certain embodiments, the atherosclerosis can be reduced in a whole aorta, an aortic sinus, an inominate artery or combinations thereof.

In various embodiments, changing the phenotype of the monocyte or macrophage from the proinflammatory M1 phenotype to the anti-inflammatory M2 phenotype can reduce plaque lipid content in an aortic sinus, an innominate artery, or both. In various embodiments, changing the phenotype of the monocyte or macrophage from the proinflammatory M1 phenotype to the anti-inflammatory M2 phenotype can reduce plaque macrophage content in an aortic sinus, an innominate artery or both.

In various embodiments, the rAAV vector can be produced by providing a first plasmid comprising ApoA-I Milano or a fragment thereof; providing a second plasmid complimentary to the first plasmid and which comprises components for rescue and packaging; co-transfecting the first plasmid and the second plasmid into a host cell; and generating a quantity of the rAAV vector from the co-transfected host cell. In various embodiments, the pair of the first plasmid and the second plasmid can be selected such that the rAAV vector is targeted for delivery to a specific tissue type. In various embodiments, the second plasmid can further comprise AAV rescue and packaging components derived from an AAV serotype selected from the group consisting of AAV1, AAV2, AAV5, AAV7, AAV8, AAV9, AAV10 and combinations thereof. Embodiments of the present invention provide for a method, comprising: measuring the expression level of one or more markers selected from the group consisting of MCP-1, IL-6, TNF-a, Arg-1, Ym-1, and CD206 to monitor monocyte or macrophage phenotypic switching in a mammal in need thereof; and determining the presence of a phenotypic switch from a proinflammatory M1 macrophage to an anti-inflammatory M2 macrophage when MCP-1, IL-6 and/or TNF-α is down-regulated, and/or Arg-1, Ym-1 and/or CD206 is up-regulated, or determining the absence of a phenotypic switch from the proinflammatory M1 macrophage to the anti-inflammatory M2 macrophage when MCP-1, IL-6 and/or TNF-a is not down-regulated, and/or Arg-1, Ym-1 and/or CD206 is not up-regulated, or determining the presence of a phenotypic switch from an anti-inflammatory M2 macrophage to a proinflammatory M1 macrophage when MCP-1, IL-6 and/or TNF is up-regulated, and/or Arg-1 and/or CD206 is down-regulated, or determining the presence of a phenotypic switch from a proinflammatory M1 macrophage to an anti-inflammatory M2 macrophage when MCP-1, IL-6 and/or TNF-a is down-regulated, and/or when, Arg-1, Ym-1 and/or CD206 is not up-regulated.

Embodiments of the present invention provide for a method for assessing the efficacy of a treatment for atherosclerosis in a mammalian subject in need thereof, comprising: determining the phenotype of the macrophages in the mammalian subject; and making a determination that a treatment is providing beneficial results to a mammalian subject if a phenotypic switch from proinflammatory M1 macrophage to anti-inflammatory M2 macrophage is detected, or making a determination that a treatment is not providing beneficial results to the mammalian subject if a phenotypic switch from anti-inflammatory M2 macrophage to proinflammatory M1 macrophage is detected. In various embodiments, the treatment for atherosclerosis is treatment with ApoA-1 Milano.

Other features and advantages of the invention will become apparent from the following detailed description, taken in conjunction with the accompanying drawings, which illustrate, by way of example, various features of embodiments of the invention.

DESCRIPTION OF THE INVENTION

Figure 1:
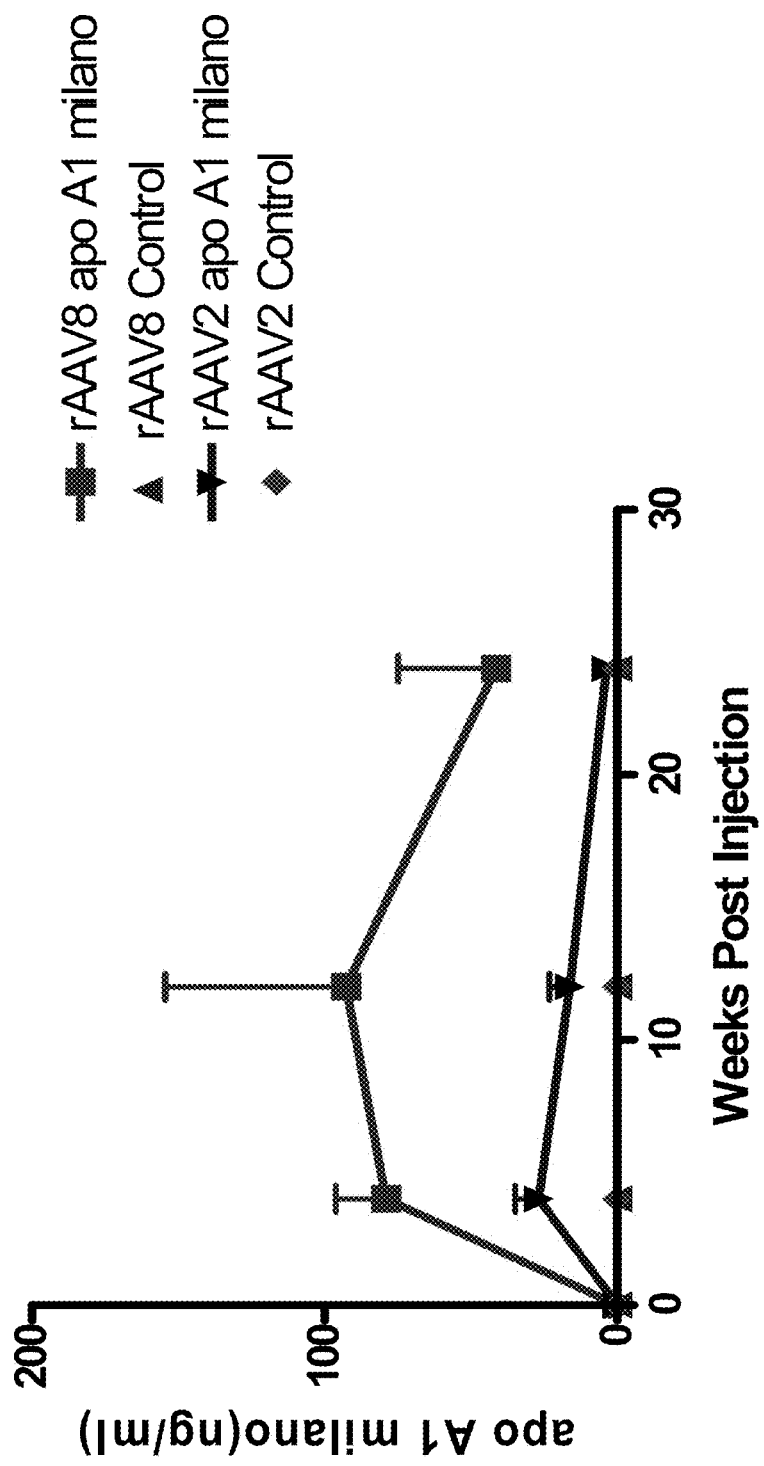
FIG. 1 depicts expression of apo A1 Milano in the mice with rAAV in accordance with various embodiments of the present invention. Serum Levels of apo A1 Milano at 4, 12, 24 weeks after injection virus and a group of mice with the empty vector is used as a control. The data represent mean±SD from 12 mice per group. These data, analyzed by Student's unpaired t-test, show there was statistically significant difference among AAV8 apo A1 Milano and another three groups. P—Value rAAV8/Apo A1 Milano vs rAAV8 Control: <0.001; rAAV2/Apo A1 Milano vs rAAV2 control: <0.001:rAAV8/Apo A1 Milano vs rAAV2 Apo A1 Milano: <0.001.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, reducing the likelihood of the disease condition worsening, curing the disease condition and prolonging a patient's life or life expectancy.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

"Vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

"AAV vector" refers to any vector derived from any adeno-associated virus serotype, including, without limitation, AAV-1, AAV-2, AAV-3, AAV-4, AAV-5, AAV-7, AAV-8, AAV-9, and AAV-10 and the like. AAV vectors can have one or more of the AAV wild-type genes deleted in whole or in part, preferably the Rep and/or Cap genes, but retain functional flanking ITR sequences. Functional ITR sequences are generally necessary for the rescue, replication, packaging and potential chromosomal integration of the AAV genome. Thus, an AAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging.

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious. In addition, the AAV capsid protein coat can be from any of the various AAV serotypes depending on the target of the AAV virion.

A "recombinant AAV virion" or "rAAV virion" is defined herein as an infectious, replication-defective virus composed of an AAV protein shell, encapsidating a heterologous DNA molecule of interest (e.g., genes encoding ApoA-I Milano) which is flanked on both sides by AAV ITRs. A rAAV virion may be produced in a suitable host cell which has had an AAV vector, AAV Rep and Cap functions and helper virus functions introduced therein. In this manner, the host cell is rendered capable of producing AAV replication and capsid proteins that are required for replicating and packaging the AAV vector (i.e., containing a recombinant nucleotide sequence of interest) into recombinant virion particles for subsequent gene delivery. The complete transgene may consist of a promoter, the coding sequences, usually a cDNA and a polyadenylation signal. A transgene may also include regulatory sequences and intron regions. Promoters that would regulate transgene expression may include constitutive, inducible and tissue-specific promoters.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via any method of gene delivery, including replication-defective viral vectors, such as via a rAAV.

The term "heterologous," as it relates to nucleic acid sequences such as gene sequences and control sequences, denotes sequences that are not normally joined together and/or are not normally associated with a particular virus. Allelic variation or naturally occurring mutational events do not give rise to heterologous DNA, as used herein.

"DNA" is meant to refer to a polymeric form of deoxyribonucleotides (i.e., adenine, guanine, thymine and cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the non-transcribed strand of DNA (i.e., the strand having the sequence homologous to the mRNA). The term captures molecules that include the four bases adenine, guanine, thymine and cytosine, as well as molecules that include base analogues which are known in the art.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences; although one of skill in the art will readily appreciate that various polynucleotides do not operate in this fashion (e.g., antisense RNA, siRNA, ribozymes, wherein the RNA transcript is the product). With respect to protein products (i.e., not RNA products), the boundaries of the coding sequence are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence. Moreover, a "gene" (i) starts with a promoter region containing multiple regulatory elements, possibly including enhancers, for directing transcription of the coding region sequences; (ii) includes coding sequences, which start at the transcriptional start site that is located upstream of the translational start site and ends at the transcriptional stop site, which may be quite a bit downstream of the stop codon (a polyadenylation signal is usually associated with the transcriptional stop site and is located upstream of the transcriptional stop); and (iii) may contain introns and other regulatory sequences to modulate expression and improve stability of the RNA transcript.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

"Homology" and "homologous" as used herein refer to the percent of identity between two polynucleotide or two polypeptide moieties. The correspondence between the sequences from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA or two polypeptide sequences are "substantially homologous" to each other when at least about 80%, preferably at least about 90%, and most preferably at least about 95% of the nucleotides or amino acids, respectively, match over a defined length of the molecules, as determined using the methods above.

"Isolated" as used herein when referring to a nucleotide sequence, vector, etc., refers to the fact that the indicated molecule is present in the substantial absence of other biological macromolecules of the same type. Thus, an "isolated nucleic acid molecule which encodes a particular polypeptide" refers to a nucleic acid molecule that is substantially free of other nucleic acid molecules that do not encode the subject polypeptide. Likewise, an "isolated vector" refers to a vector that is substantially free of other vectors that differ from the subject vector. However, the subject molecule or vector may include some additional bases or moieties that do not deleteriously affect the basic characteristics of the composition.

"Purified" as used herein when referring to a vector, refers to a quantity of the indicated vector that is present in the substantial absence of other biological macromolecules. Thus, a "purified vector" refers to a composition that includes at least 80% subject vector, preferably at least 90%, 91%, 92%, 93%, 94%, 95%, 96%, 97%, 98% or 99% subject vector with respect to other components of the composition "Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

Described herein, the inventors evaluated the effects of intravenously administered rAAV8 encoding Apo A-I Milano on aortic and innominate artery atherosclerosis, plaque composition and phenotype of circulating mononuclear cells in Apo E−/− Apo A1−/− mice.

The inventors found that rAAV8 mediated Apo A-I Milano gene transfer reduces all plaques; for example, plaque in whole aorta, aortic sinuses and innominate arteries. The plaque that remains is more table and less likely to rupture and trigger a blood clot. Further, the inventors evaluated the effects of rAAV2 mediated Apo A-I Milano gene transfer using a single intramuscular injection, on murine atherosclerosis and macrophage phenotype. The inventors also found that a single intramuscular injection of rAAV2-Milano significantly reduces aortic atherosclerosis despite absence of detectable levels of circulating transgene; these effects are associated with adoption of an anti-inflammatory phenotype in macrophages. As such, various embodiments of the present invention are based, at least in part, upon these findings.

Various embodiments of the present invention provide for a method of changing the phenotype of monocytes and macrophages from a proinflammatory M1 phenotype to an anti-inflammatory M2 phenotype. In various embodiments, the method comprises providing a composition comprising a recombinant adeno-associated virus (rAAV) vector comprising an exogenous gene encoding ApoA-I Milano or a fragment thereof; and administering the composition to a mammal in need thereof to change the phenotype of monocytes or macrophages from a proinflammatory M1 phenotype to an anti-inflammatory M2 phenotype.

In various embodiments, the method further comprises monitoring monocyte or macrophage phenotypic switching in the mammal. In other embodiments, the method further comprises assessing the efficacy of a treatment for atherosclerosis in the mammal.

In various embodiments the rAAV vector is produced by the process of: (i) providing a first plasmid that comprises ApoA-I Milano or a fragment thereof, (ii) providing a second plasmid that is complementary to the first plasmid and which comprises components for rescue and packaging, (iii) co-transfecting the first and second plasmids into a host cell, and (iv) generating a quantity of said rAAV vector from said co-transfected host cell, wherein the pair of said first and second plasmids is selected such that said rAAV vector is targeted for delivery to a specific tissue type.

In various embodiments, the second plasmid further comprises AAV rescue and packaging components derived from an AAV serotype selected from the group consisting of AAV1, AAV2, AAV5, AAV7, AAV8, AAV9, AAV10 and combinations thereof.

In various embodiments, the recombinant adeno-associated virus (rAAV) vector, comprising an exogenous gene encoding ApoA-I Milano or a fragment thereof is rAAV8 vector comprising an exogenous gene encoding ApoA-I Milano or a fragment thereof. In various embodiments the recombinant adeno-associated virus (rAAV) vector, comprising an exogenous gene encoding ApoA-I Milano or a fragment thereof is rAAV2 vector comprising an exogenous gene encoding ApoA-I Milano or a fragment thereof.

In various embodiments, the monocyte or macrophage is a circulating monocyte or macrophage. In other embodiments, the monocyte or macrophage is a peritoneal monocyte or macrophage. In various embodiments, very low levels of circulating transgene product are present. In various embodiments, changing monocyte or macrophage phenotype inhibits atherosclerosis.

In certain embodiments, changing the phenotype of monocytes or macrophages from a proinflammatory M1 phenotype to an anti-inflammatory M2 phenotype reduces atherosclerosis. In particular embodiments, changing the phenotype of monocytes or macrophages from a proinflammatory M1 phenotype to an anti-inflammatory M2 phenotype reduces atherosclerosis in whole aorta. In particular embodiments, changing the phenotype of monocytes or macrophages from a proinflammatory M1 phenotype to an anti-inflammatory M2 phenotype reduces atherosclerosis in aortic sinuses. In particular embodiments, changing the phenotype of monocytes or macrophages from a proinflammatory M1 phenotype to an anti-inflammatory M2 phenotype reduces atherosclerosis in the innominate artery.

In various embodiments changing the phenotype of monocytes or macrophages from a proinflammatory M1 phenotype to an anti-inflammatory M2 phenotype reduces plaque.

In various embodiments, changing the phenotype of monocytes or macrophages from a proinflammatory M1 phenotype to an anti-inflammatory M2 phenotype reduces plaque lipid content in aortic sinuses. In various embodiments, changing the phenotype of monocytes or macrophages from a proinflammatory M1 phenotype to an anti-inflammatory M2 phenotype reduces plaque lipid content in the innominate artery. In various embodiments, changing the phenotype of monocytes or macrophages from a proinflammatory M1 phenotype to an anti-inflammatory M2 phenotype reduces plaque macrophage content in aortic sinuses. In various embodiments, changing the phenotype of monocytes or macrophages from a proinflammatory M1 phenotype to an anti-inflammatory M2 phenotype reduces plaque macrophage content in innominate arteries.

Various embodiments of the present invention provide for monitoring macrophage phenotypic switching in a mammalian subject in need thereof. In various embodiments, the phenotypic switch is between a proinflammatory M1 macrophage and an anti-inflammatory M2 macrophage. In various embodiments, the mammalian subject has atherosclerosis. In various embodiments, the mammalian subject is or has been treated with apo A1 Milano. In various embodiments, the method comprises measuring the expression level of one or more markers selected from the group consisting of MCP-1, IL-6, TNF-a, Arg-1, Ym-1 and CD206;

and (a) determining the presence of a phenotypic switch from proinflammatory M1 macrophage to anti-inflammatory M2 macrophage when MCP-1, IL-6 and/or TNF-a is down-regulated, and/or Arg-1, Ym-1 and/or CD206 is up-regulated, or (b) determining the absence of a phenotypic switch from proinflammatory M1 macrophage to anti-inflammatory M2 macrophage when MCP-1, IL-6 and/or TNF-a is not down-regulated, and/or Arg-1, Ym-1 and/or CD206 is not up-regulated, or (c) determining the presence of a phenotypic switch from anti-inflammatory M2 macrophage to proinflammatory M1 macrophage when MCP-1, IL-6 and/or TNF is up-regulated, and/or Arg-1, Ym-1 and/or CD206 is down-regulated. Measuring the expression level of the one or more markers can be performed by any method known in the art.

Various embodiments of the present invention provide for assessing the efficacy of the treatment of atherosclerosis in a mammalian subject in need thereof. In various embodiments, the treatment of atherosclerosis is treatment with apo A1 Milano. The method comprises: determining the phenotype of the macrophages in the mammalian subject; and (a) making a determination that the treatment is providing beneficial results to the mammalian subject if a phenotypic switch from proinflammatory M1 macrophage to anti-inflammatory M2 macrophage is detected, or (b) making a determination that the treatment is not providing beneficial results to the mammalian subject if a phenotypic switch from anti-inflammatory M2 macrophage to proinflammatory M1 macrophage is detected.

In various embodiments, the treatment with apo A1 Milano may be provided in variety of ways known in the art. Examples include, but are not limited to IM or IV rAAV gene transfer (e.g., rAAV serotype 2, rAAV serotype 8), administration of a composition comprising apo A1 Milano protein, administration of a composition comprising apo A1 Milano protein via a drug eluting stent.

In various embodiments, the vectors of the present invention are based on the vector described in U.S. Pat. No. 5,474,935, with the transgene being ApoA-I Milano or a fragment thereof, for changing the phenotype of monocytes and macrophages from a proinflammatory M1 phenotype to an anti-inflammatory M2 phenotype and the treatment of atherosclerosis. Preparation of rAAV vectors can be as described in Chatterjee, S. & K. K. Wong, Adeno-associated virus vectors for the delivery of ribozymes. In "Intracellular Ribozyme Applications: Principles and Protocols," J J Rossi and L. Couture (Eds.), Horizon Scientific Press, pp. 189-215 (2000); Chatterjee, S. et al., "Transduction of primitive human marrow and cord blood-derived hematopoietic progenitor cells with adeno-associated virus vector," Blood, Vol. 93, pp. 1882-1894 (1999). Transgene delivery systems have frequently included the use of the CMV immediate early promoter (Fitzsimons, H. L. et al., "Promoters and regulatory elements that improve adeno-associated virus transgene expression in the brain," Methods, Vol. 28, pp. 227-36 (2002); Phillips, M. I., "Gene therapy for hypertension: sense and antisense strategies," Expert Opin Biol Ther, Vol. 1, pp. 655-62 (2001); Smith, L. C. et al., "Advances in plasmid gene delivery and expression in skeletal muscle," Curr Opin Mol Ther, Vol. 2, pp. 1504 (2000); Keating, A. et al., "Effect of different promoters on expression of genes introduced into hematopoietic and marrow stromal cells by electroporation," Exp Hematol, Vol. 18, pp. 99-102 (1990); Muller, S. R. et al., "Efficient transfection and expression of heterologous genes in PC12 cells," DNA Cell Biol, Vol. 9, pp. 221-9 (1990)) since it is one of the most active promoters among viral and eukaryotic species without a specific host cell type requirement. However, any number of promoters may be used in constructing the rAAV vectors of the present invention as will be recognized by one of skill in the art. For example, the rAAV-5 vector used in the present invention incorporates a CBA promoter.

The construction of the vectors of the present invention can be completed by widely recognized means for manufacturing AAV virions, which entails co-transfection of a host cell with two different, yet complementing plasmids. One of these contains the therapeutic or reporter transgene sandwiched between the two cis acting AAV ITRs. The AAV components that are needed for rescue and subsequent packaging of progeny recombinant genomes are provided in trans by a second plasmid encoding the viral open reading frames for rep and cap proteins. However, any number of other techniques for construction of the vectors of the present invention may be used as will be recognized by one of skill in the art. See, e.g. Gao, G. (2002) Proc Natl Acad Sci USA 99:11854-11859; Hauck, B. (2003) Journal of Virology 77(4):2768-2774; Gao, G. (2004) Journal of Virology 78(12):6381-6388. Still other methods may be used for construction of the vectors of the present invention, for example, U.S. Pat. No. 5,658,776 refers to packaging systems and processes for packaging AAV vectors that replace the AAV P5 promoter with a heterologous promoter. Alternatively, U.S. Pat. No. 5,622,856 refers to constructs and methods for AAV vector production, which provide constructs formed by moving the homologous P5 promoter to a position 3' to the rep genes, and optionally flanking the rep-cap and repositioned P5 promoter with FRT sequences.

Furthermore, in various embodiments of the invention, the ITRs and portions of the genome of the first plasmid and the rep and cap proteins of the second plasmid can be derived from any serotype of AW vector. In this way, the rAAV virions of the present invention can be specifically tailored to target a subject tissue with greater specificity. It is well known in the art that AAV serotype has a significant impact on tissue-specific gene expression (Hauck, B. et al., "Generation and characterization of chimeric recombinant AAV vectors," Mol Ther, Vol. 7, pp. 419-25 (2003); Chao, H. et al., "Several log increase in therapeutic transgene delivery by distinct adeno-associated viral serotype vectors," Mol Ther, Vol. 2, pp. 619-23 (2000); Xiao, W. et al., "Gene therapy vectors based on adeno-associated virus type 1," J Virol, Vol. 73, pp. 3994-4003 (1999); Rabinowitz, J. E. et al., "Cross-packaging of a single adeno-associated virus (AAV) type 2 vector genome into multiple AAV serotypes enables transduction with broad specificity," J Virol, Vol. 76, pp. 791-801 (2002); Alisky, J. M. et al., "Transduction of murine cerebellar neurons with recombinant FIV and AAV5 vectors," Neuroreport, Vol. 11, pp. 2669-73 (2000); Chiorini, J. A. et al., "Cloning and characterization of adeno-associated virus type 5," J Virol, Vol. 73, pp. 1309-19 (1999); Davidson, B. L. et al., "Recombinant adeno-associated virus type 2, 4, and 5 vectors: transduction of variant cell types and regions in the mammalian central nervous system," Proc Nat Acad Sci USA, Vol. 97, pp. 3428-32 (2000); Rutledge, E. A. et al., "Infectious clones and vectors derived from adeno-associated virus (AAV) serotypes other than AAV type 2," J Virol, Vol. 72, pp. 309-19 (1998)). For example, the DNA element of the first plasmid may be derived from one AAV serotype, the rep proteins may be derived from another AAV serotype, and the cap proteins may be derived from still another AAV serotype. In particular, the AAV vector genome can be pseudotyped by packaging with capsids from different AAV serotypes, which has been effective in directing rAAV gene therapies to specific tissues (Weitzman, M. et al., "Breaking the barriers to global gene delivery," Nature Biotechnology, Vol. 23, Issue 3, pp. 305-306 (2005); Wang, Z. et al., "Adeno-associated virus serotype 8 efficiently delivers genes to muscle and heart," Nature Biotechnology, Vol. 23, Issue 3, pp. 321-328 (2005); Wang, L. et al., "Sustained correction of disease in naive and AAV2-pretreated hemophilia B dogs: AAV2/8-mediated, liver-directed gene therapy," Gene Therapy, Vol. 105, Issue 8, pp. 3079-3086 (2005)). In various embodiments of the present invention, capsids derived from AAV serotypes 1, 8, 9 and 10 may be particularly effective in intramuscular injections. Further, capsids derived from AAV serotypes 1, 7 and 8 may be particularly effective for hematopoietic stem cell transduction. Still further, capsids derived from AAV serotype 8 may be particularly effective targeting the liver.

Various embodiments of the present invention also relate to the treatment, prevention, inhibition, stabilization and/or induction of regression of atherosclerosis, as well as the treatment, prevention, inhibition and/or stabilization of any disease or physiological condition in which atherosclerosis (or atherogenesis) plays a role. Furthermore, the methods of the present invention may be particularly useful in treating atherosclerosis when caused by invasive techniques, such as percutaneous transluminal coronary angioplasty ("PTCA"); insertion of a bypass graft or stent insertion; treatment of restenosis following stent placement; or as a result of bypass graft insertion. Each of the aforementioned applications is contemplated as being within the scope of the present invention. Still further, other diseases and physiological conditions that may benefit from the methods of the present invention will be readily apparent to those of skill in the art, and are also contemplated as being within the ambit of the present invention.

Various embodiments of the present invention are also based on a gene therapeutic approach to the treatment of coronary heart disease and/or vascular disease. In some embodiments of the invention, rAAV virions including heterologous DNA corresponding to an ApoA-I Milano coding sequence are generated by any conventional technique known in the art. By way of example, the recombinant AAV virions of the present invention, including the ApoA-I Milano DNA of interest, can be produced by a standard methodology that generally involves the steps of: (1) introducing an AAV vector plasmid into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient rAAV virion production in the host cell; and (4) culturing the host cell to produce rAAV virions. The AAV vector, AAV helper construct and the helper virus or accessory function vector(s) can be introduced into the host cell either simultaneously or serially, using standard transfection techniques. Any number of other approaches may also be used, as will be readily recognized by one of skill in the art.

AAV vectors are constructed using known techniques to at least provide, as operatively linked components in the direction of transcription, (a) control elements including a transcriptional initiation region, (b) the ApoA-I Milano DNA of interest and (c) a transcriptional termination region. Moreover, any coding sequence sufficiently homologous to the ApoA-I Milano coding sequence so as to exhibit functional properties substantially similar to the ApoA-I Milano coding sequence may be used in connection with alternate embodiments of the present invention. The control elements are selected to be functional in the targeted cell(s). The resulting construct, which contains the operatively linked components, may be bounded (5' and 3') with functional AAV ITR sequences. The nucleotide sequences of AAV ITR regions are known. See, e.g., Kotin, R. M. (1994) Human Gene Therapy 5:793-801; Berns, K. I., "Parvoviridae and their Replication" in Fundamental Virology, $2^{nd}$ Edition, (B. N. Fields and D. M. Knipe, eds.) for the AAV-2 sequence. AAV ITRs used in the vectors of the invention need not have a wild-type nucleotide sequence, and may be altered (e.g., by the insertion, deletion or substitution of nucleotides). Additionally, AAV ITRs may be derived from any of several AAV serotypes, including, without limitation, AAV-1, AAV-2, AAV-3, AAV-4, AAV-5, AAV-7, AAV-8, AAV-9, AAV-10 and the like. See, e.g. Gao et al., J. Virol. 2004 June; 78(12):6381-8; Weitzman, M. et al. (2005); Wang, Z. et al. (2005); and Wang, L. et al. (2005). Furthermore, 5' and 3' ITRs that flank a selected nucleotide sequence in an AAV expression vector need not necessarily be identical or derived from the same AAV serotype or isolate, so long as they function as intended (i.e., to allow for excision and replication of the bounded ApoA-I Milano nucleotide sequence of interest).

The rAAV genome encoding the ApoA-I Milano transgenes within AAV ITRs may be packaged in virion capsids derived from any AAV serotype including AAV-1, AAV-2, AAV-4, AAV-5, AAV-6, AAV-7, AAV-8, AAV-9, AAV-10 and the like. See, e.g. Gao et al. (2004); Weitzman, M. et al. (2005); Wang, Z. et al. (2005); and Wang, L. et al. (2005).

The virions described above are useful for changing the phenotype of monocytes and macrophages from a proinflammatory M1 phenotype to an anti-inflammatory M2 phenotype, for treating atherosclerosis, for reducing plaque, as well as for preventing and treating coronary heart disease and/or vascular disease and thus are useful for the manufacture of pharmaceutical compositions which contain an effective amount of rAAV-ApoA-I Milano vectors in admixture with inorganic or organic, solid or liquid, pharmaceutically acceptable carriers. Thus, another aspect of this invention is a composition for changing the phenotype of monocytes and macrophages from a proinflammatory M1 phenotype to an anti-inflammatory M2 phenotype, for treating atherosclerosis, for reducing plaque, as well as for preventing and treating coronary heart disease and/or vascular disease described herein in combination with a pharmaceutically acceptable excipient.

The pharmaceutical compositions according to the invention are those which are suitable for oral, transdermal, topical, or parenteral, such as intramuscular or intravenous, administration to humans, and which contain the pharmacologically active rAAV transfected vectors together with a pharmaceutically acceptable carrier. The dosage depends on various factors such as the age, weight, severity of vascular condition, and other factors a doctor might identify.

In certain embodiments, the therapeutic compositions are administered via suppository, or in tablet or capsule formulations for oral delivery. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, enterics, sustained release formulations, powders, and the like. Oral formulations for gene therapy are known in the art. See, e.g. Chen, J. et al. (2004) World J. Gastroenterol 10(1):112-116. Further, other oral formulations are contemplated for use in the present invention as will be recognized by one of skill in the art.

Additional formulations which are suitable for other modes of administration, such as transdermal and topical administration, include salves, tinctures, creams, lotions, transdermal patches, transplanted skin, genetically engineered skin, stent coatings and suppositories. For salves and creams, traditional binders, carriers and excipients may include, for example, polyalkylene glycols or triglycerides. In certain embodiments, a transdermal patch may be used for delivering therapeutics. See, e.g. U.S. Pat. No. 4,638,043. Transdermal and topical formulations for gene therapy are known in the art. See, e.g. Jensen, T G (2004) Expert Opin Biol Ther. 4(5):677-82. Further, other transdermal and topical formulations are contemplated for use in the present invention as will be recognized by one of skill in the art.

Particularly suitable dosage forms for parenteral administration are sterile aqueous solutions of the pharmacologically active rAAV transfected vectors in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the pharmacologically active rAAV transfected vectors, with or without adjuvants, can also be in lyophilized form and brought into solution prior to parenteral administration by the addition of suitable solvents.

Generally, an injectable composition of the invention may be a solution that is ready for injection, or a dry soluble composition that is ready to be combined with a solvent just prior to use, or a liquid concentrate ready for dilution prior to administration. In preparing a composition for injection strict attention must be paid to tonicity adjustment to avoid irritation.

The vehicle normally has no therapeutic activity and is nontoxic, but presents the pharmacologically active rAAV transfected vectors to the body tissues or circulation in a form appropriate for absorption. Absorption normally will occur most rapidly and completely when the pharmacologically active rAAV transfected vectors is presented as an aqueous solution. However, modification of the vehicle with water-miscible liquids or substitution with water-immiscible liquids can affect the rate of absorption. In preparing the compositions which are suitable for subcutaneous injection, one can use aqueous vehicles, water-miscible vehicles, and nonaqueous vehicles. Certain aqueous vehicles are recognized officially because of their valid use in parenterals generally.

Water-miscible vehicles are also useful in the formulation of the parenteral composition of this invention. These solvents are used primarily to affect the solubility of the pharmacologically active rAAV transfected vectors. These solvents may include, for example, ethyl alcohol, polyethylene glycol and propylene glycol.

Additional substances may be included in the injectable compositions of this invention to improve or safeguard the quality of the composition. Thus, an added substance may affect solubility, provide for patient comfort, enhance the chemical stability, or protect preparation against the growth of microorganisms. Thus, the composition may include an appropriate solubilizer, substances to make a solution isotonic, substances to act as antioxidants, and substances that act as a preservative to prevent the growth of microorganisms. These substances will be present in an amount that is appropriate for their function, but will not adversely affect the action of the composition as a treatment for disease conditions as contemplated herein.

Generally, the sterile, parenterally injectable composition of this invention and other therapeutic formulations suitable for delivery to a mammal in accordance with various embodiments of the present invention can be readily prepared by routine experimentation by the skilled artisan. Guidance as to suitable pharmaceutical formulations is provided by Remington: The Science and Practice of Pharmacy 19$^{th}$ Ed.

In accordance with an embodiment of the invention, the rAAV virions encoding ApoA-I Milano are delivered to a mammal in a sufficient quantity and by a sufficient delivery route so as to effect gene transfer. As described in the ensuing Examples, this provides an effective way for changing the phenotype of monocytes and macrophages from a proinflammatory M1 phenotype to an anti-inflammatory M2 phenotype, for treating atherosclerosis, for reducing plaque, and an effective treatment for atherosclerosis in mammals. In various embodiments, a sufficient and therapeutic quantity may be from about $1 \times 10^{10}$ vector genome/kg to about $1 \times 10^{14}$ vector genome/kg of rAAV-ApoA-I Milano vectors in vivo. In one embodiment of the present invention, the ApoA-I Milano vector may be delivered to a subject by first transducing multipotent stem cells (e.g., bone marrow cells, blood stem cells, stromal cells, mesenchymal stem cells, etc.) with a quantity of the rAAV-ApoA-I Milano vector, and then transplanting these cells into a mammal. In an alternate embodiment, the rAAV-ApoA-I Milano vector may be introduced into a mammal by direct intramuscular or intravenous injection, or directly into the artery at the site of PTCA or stent placement by any conventional methodology, as will be readily appreciated by one of skill in the art. This results in secretion of ApoA-I Milano either directly into the circulation or locally in atherosclerotic plaque areas. Further, the rAAV virions of the present invention can be delivered as a single administration or as a treatment regimen, e.g., daily, weekly, or at any other suitable time interval, as will be readily recognized by one of skill in the art. In another embodiment of the present invention, one serotype of rAAV virion can be delivered as a single administration followed by delivery of a different serotype of rAAV virion.

The present invention is also directed to a kit for changing the phenotype of monocytes and macrophages from a proinflammatory M1 phenotype to an anti-inflammatory M2 phenotype, for treating atherosclerosis, for reducing plaque, and for the treatment of atherosclerosis and related disease conditions in a subject. The kit is an assemblage of materials or components, including at least one means of effecting gene transfer of ApoA-I Milano in a subject in accordance with various embodiments of the present invention. The exact nature of the components configured in the inventive kit depends on its intended purpose and on the particular methodology that is employed. For example, some embodiments of the kit are configured for changing the phenotype of monocytes and macrophages from a proinflammatory M1 phenotype to an anti-inflammatory M2 phenotype. Other embodiments of the kit are configured for the purpose of treating atherosclerosis and/or related disease conditions in a mammalian subject. Still other embodiments are configured for the purpose of preventing the onset of atherosclerosis that is the result of another therapy, e.g., angioplasty or stent placement. In one embodiment, the kit is configured particularly for the purpose of treating human subjects.

Instructions for use may be included with the kit. "Instructions for use" typically include a tangible expression describing the preparation of virions and/or at least one method parameter, such as the relative amounts of rAAV-ApoA-I Milano vector genome, dosage requirements and administration instructions, and the like, typically for an intended purpose. Optionally, the kit also contains other useful components, such as, diluents, buffers, pharmaceutically acceptable carriers, specimen containers, syringes, stents, catheters, and pipetting or measuring tools.

The materials or components assembled in the kit can be provided to the practitioner stored in any convenient and suitable ways that preserve their operability and utility. For example the components can be in dissolved, dehydrated, or lyophilized form; they can be provided at room, refrigerated, or frozen temperatures. The components are typically contained in suitable packaging material(s). As employed herein, the phrase "packaging material" refers to one or more physical structures used to house the contents of the kit. The packaging material is constructed by well known methods, preferably to provide a sterile, contaminant-free environment. The packaging materials employed in the kit are those customarily utilized in the field. As used herein, the term "package" refers to a suitable solid matrix or material such as glass, plastic, paper, foil, and the like, capable of holding the individual kit components. Thus, for example, a package can be a glass vial used to contain suitable quantities of a composition containing a volume of rAAV-ApoA-I Milano vector. The packaging material generally has an external label which indicates the contents and/or purpose of the kit and/or its components.

The tools, kits, and methods of the present invention may be implemented in connection with a gene therapeutic approach for treating atherosclerosis and related disease conditions, or in connection with monitoring phenotypic switches. The various embodiments of the present invention may therefore provide a means for prevention or reduction of the likelihood of the aforementioned disease conditions. The embodiments of the invention are also suitable for use in connection with monitoring the success of ongoing or completed therapeutic intervention. For instance, a subject's serum may be tested prior to treatment to screen for circulating levels of ApoA-I Milano; during the course of treatment (e.g., to enhance a physician's ability to implement an effective treatment regimen); and/or following the completion of an intervention to determine a level of success (e.g., lifestyle changes, angioplasty and bypass surgery).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Mice received one intravenous injection of $1.2 \times 10^{12}$ vector genome copies of rAAV8-Milano or rAAV8-Control (12 mice per group). Four weeks after injection, mice were placed on high fat diet. Twenty weeks later mice were euthanized and the extent of atherosclerosis in the en fasse aorta, aortic sinuses and innominate artery was measured. Oil-red O staining and Moma-2 staining were used to measure lipid content and macrophage content of the plaques respectively. Quantitative PCR (qPCR) was used to analyze phenotype of macrophages.

Example 2

Compared to vector control, rAAV 8 Milano recipients had less atherosclerosis in whole aorta (13.4±1.1% vs. 7.7±0.06%, p=0.001), in aortic sinuses (77.1±9.6 vs 44.8±2.3, p=0.01) and in the innominate artery (12.4±2.4 vs 4.4±2.1 mm$^2$; p<0.05). These effects were associated with reduced plaque lipid content in aortic sinuses (20.3±vs 12.8±2.3, p=0.03) and in innominate artery (14.4±2.5 vs 5.3±1.6%; p=0.001) and reduced plaque macrophage content in aortic sinuses (20.9±2.1 vs 11.7±2.4%, p=0.02) and in innominate arteries (8.3±1.5 vs 3.1±1.1% p=0.01). Compared to vector control, the rAAV8 Milano recipients showed reduced expression of MCP-1 and TNF-α mRNAs (M1 markers) and increased expression of Arg-1 (M2 marker) in circulating mononuclear cells.

Example 3

ApoE-/- ApoA-/- double knockout received one intramuscular injection of $1.2 \times 10^{12}$ vector genome copies of rAAV2-Milano or rAAV2-Control (10 mice per group). Four weeks after intramuscular injection, mice were placed on high fat diet. Twenty weeks later, mice were euthanized and the expression of Apo A-I Milano mRNA in liver was measured by quantitative PCR (qPCR). In addition, the phenotype of macrophages in the liver, peritoneal macrophages, and peripheral blood mononuclear cells (PBMC) were determined by qPCR. The quantitative extent of total aorta plaques was evaluated by oil-red O staining. ELISA analysis was performed to measure serum level of the Apo A-I Milano.

Example 4

Serum Apo A-I Milano levels were not detectable in mice receiving rAAV2 Milano and in Controls; however surprisingly, significant difference was found in the extent of atherosclerosis between the two groups: 14.6±2.1 for rAAV2 control group vs. 9.3±1.0 for the rAAV2-Milano group (P=0.04). qPCR analysis of PBMC revealed that the relative expression level of MCP1, IL-6, and TNF-α mRNAs were lower and the expression level of Arg-1 as well as YM1 mRNA were higher in the rAVV2-Milano group compared to the Control group. Similarly, the level of MCP-1, IL-6, and TNF-α mRNA were lower and YM1 was higher in the liver of rAAV-2 Milano group. Likewise, the expression of MCP-1, IL-6, and TNF-α mRNAs was lower and those of YM1 and Arg-1 were higher in the peritoneal macrophages of mice injected with rAAV2-Milano compared to the Control group.

Example 5

Construction of Recombinant Adeno-Associated Virus Vectors

The construction of the rAAV vectors of the present invention are completed by co-transfecting a host cell with two different plasmids. rAAV virions are prepared with the plasmids derived from various AAV serotypes. In each of the first plasmids, ApoA-I Milano is sandwiched between the two cis acting AAV ITRs. The AAV rep and cap proteins are provided in trans by a second plasmid encoding the viral open reading frames for rep and cap proteins of AAV. In one virion, rAAV2, the first plasmid genome is derived from AAV serotype 2 and the second plasmid is derived from AAV serotype 2 (Rep2Cap2). In a second virion, rAAV5, the first plasmid genome is derived from AAV serotype 5 and the second plasmid is derived from AAV serotype 5 (Rep5Cap5). In a third virion, rAAV1, the first plasmid genome is derived from AAV serotype 2 and the second plasmid is derived from AAV serotypes 2 and 1 (Rep2Cap1). In a fourth virion, rAAV7, the first plasmid genome is derived from AAV serotype 2 and the second plasmid is derived from AAV serotypes 2 and 7 (Rep2Cap7). In a fifth virion, rAAV8, the first plasmid genome is derived from AAV serotype 2 and the second plasmid is derived from AAV serotypes 2 and 8 (Rep2Cap8). In a sixth virion, rAAV9, the first plasmid genome is derived from AAV serotype 2 and the second plasmid is derived from AAV serotypes 2 and 9 (Rep2Cap9). Other virions may be readily implemented as part of the present invention, as will be recognized by one of skill in the art.

Example 6

Production of Recombinant Adeno-Associated Virus (rAAV)

Vectors:

A rAAV viral vector plasmid was constructed based on vectors previously constructed and utilized in the inventors' laboratory for the purpose of apo A1 Milano expression. [1] The specific rAAV vector serotypes used in this study contain each AAV serotype 2 and 8 viral capsid and a single-stranded DNA containing AAV2 inverted terminal repeat and encoding the human apo A1 Milano gene cDNA driven by a cytomegalovirus (CMV) immediate-early promoter/enhancer. In addition, the enhanced green fluorescent protein (EGFP) marker gene was also included in the constructs to simplify the monitoring procedure for transgene detection.

Cultured Cells:

NautCells™ (Microbix Biosystems Inc. Canada), a reliable and traceable 293 human embryo kidney (HEK) cell clone producing a high titre of rAAV vectors, were grown and maintained in high glucose DMEM (Invitrogen) culture medium containing 10% fetal bovine serum, 100 units/ml-100 mg/ml penicillin-streptomycin in 5% $CO_2$ at 37° C.

Transfection of rAAV Using Effecten Transfection Reagent (Qiagen):

Subcultured actively growing NautCells™ were placed in 15 cm culture dishes with high glucose DMEM and incubated in 5% $CO_2$ at 37° C. overnight. The medium was changed the next day and used for transfection 2-4 h. A plasmid mixture consisting of 4 ug of rAAV vector (individual constructs), 4 ug of AAV packaging plasmid XX2 (AAV rep2 and cap2) or p5E18-VD287 (AAV rep2 and cap8), and 12 mg of adenovirus helper plasmid XX6-80 were mixed with EC buffer (Qiagen Inc., Valencia, Calif.) to a final volume of 700 ul. Enhancer (120 ul; Qiagen Inc.) was added to each tube and vortexed immediately for 10 s. The tubes were placed at room temperature for 10 min. Fresh DMEM culture medium (4 ml) was added to each individual tube and mixed by pipetting up and down three times. The medium was then laid drop-wise onto NautCell™ while the dish was gently swirled. Transfected NautCells™ were scraped with a cell lifter at 66-72 h post-transfection in the presence of medium. The cells from five dishes were combined in a 50 ml disposable centrifuge tube, collected by spinning in Sorvall TC centrifuge at 1,000 rpm for 8 min at RT. The media are discarded, and the cell pellets were stored at −80° C. for later use.

Purification of rAAV Virus Using Discontinuous Iodixanol Density Gradients:

The cell pellets were resuspended in 1.5 ml of 150 mM NaCl, 50 mM Tris-HCl, pH 8.5. The cells subjected to five cycles of freezing (dry ice-ethanol bath) and thawing (37° C. water bath) with vortexing for 30 s after each thawing. The lysed cells were incubated with 0.5% deoxycholate (Fluka) in the presence of 50 u/ml Benzonase (Sigma) at 37° C. for 30 min. The lysate was clarified and recovered by centrifugation at 4500 g at 4° C. for 20 min. Purification of rAAV particles was accomplished by discontinuous iodixanol density gradient centrifugation method as previously described by Muzyczka et al. [2]. The virus was concentrated and desalted by centrifugation through the Amicon ultre-15 centrifugal filter devices (Millipore 100K NMWL device).

Dot Blot Hybridization for Determining rAAV Vector Genome (VG) Titers and rAAV Transduction Assay for Determining Transducing Units (TU):

rAAV vector genome titers were determined by dot-blot assay using RNA Detector Northern Blotting Kit (KPL) according to the manufacturer's instructions, and the titers were rAAV2/2 6.2×10e12 genome copies/ml, rAAV2/8 5.6× 19e12 genome copies/ml. Viral transducing units (Tu) were measured by transduction of 293 cells in the presence of adenovirus helper with MOI followed by FACS.

Example 7

Animal Procedures and Study Design

Animal Procedures:

The apo A-1/apoE double-knockout mice on C57BL/6 background were kindly provided by Dr. Linda Curtiss (Department of Immunology, The Scripps Research Institute, La Jolla, Calif.) and maintained as a breeding colony. Mice 6-8 weeks old weighing 15-21 g were used for this study and males and females were equally represented. The animals were randomly divided into 6 groups (Table 1) and injected virus at a doses of 1.2×10e12 genome copies in 320 ul PBS (IV) 150 ul PBS (IM) per mouse, tail vein injection and intramuscular injection into the hind leg. Animals injected viruses four weeks later were placed on a high fat diet (HFD) containing 15.8% fat and 1.25% cholesterol for 24 weeks thereafter and were then sacrificed. Blood samples were periodically collected from the retro-orbital plexus at least four times before and at designated time-points after gene transfer. The use of experimental animals was in accordance with the guidelines of the CSHS Institutional Animal Care and Uses Committee.

Study Design

TABLE 1

Experimental design

| Serotype | Transgene | Route of injection | No. of mice tested |
|---|---|---|---|
| rAAV8 | EGFP-apo A1 Milano | IV tail-vein | 12 |
| rAAV8 | EGFP | IV tail-vein | 12 |
| rAAV2 | EGFP-apo A1 Milano | IV tail-vein | 12 |
| rAAV2 | EGFP | IV tail-vein | 12 |
| rAAV2 | EGFP-apo A1 Milano | IM hind leg | 12 |
| rAAV2 | EGFP | IM hind leg | 12 |

IV: intravenous
IM: intramuscular
rAAV vector administration into apoE/apoA1 double KO mice. Serotypes 8 and 2 expressing EGFP-apo A1 Milano and EGFP(vector control) cDNA were evaluated in mice. Details of the total number of mice tested, routes of vector administration are listed.

Example 8 rAAV Biodistribution and Transduction Efficacy In Vivo Though Detection of Transgene Apo A1 Milano mRNA Expression Using RT-PCR At 24 weeks after administration, a single mouse was killed for each rAAV vector and dose group. Total RNA (n=3 mice per group) was extracted from brain, lung, heart, liver, spleen, kidney, intestine and muscle with TRIzol reagent (Invitrogen) according to the manufacturer's protocol. First-strand cDNA was synthesized from 2 ug of total RNA in a final volume 20 ul using a Omniscript Reverse Transcription Kit (Qiagen, Valencia, Calif., USA). The cDNA was used. Real-time quantitative PCR analysis using an iO5 Real-Time PCR Detection System (Bio-Rad Laboratories, Hercules, Calif., USA). For real-time PCR, all reactions were performed in triplicate, in a total reaction volume of 25 ul. The PCR was performed with the following primer sequences for human apo A1 Milano: 5'-tggatgtgct-caaagacagc-3' sense (SEQ ID NO:1) and 5'-aggccctctgtctc-cttttc-3' antisense (SEQ ID NO:2). Primers for mouse GAPDH were as follows: forward, 5' atcactgccacccagaagac-3' (SEQ ID NO:3); reverse, 5'-cacattgggggtaggaacac-3' (SEQ ID NO:4). The cycling conditions were an initial denaturation for 3 min at 94° C. followed by 35 cycles of 94° C. for 30 s, 60° C. for 20 s, and 72° C. for 20 s, which concluded by the melting curve analysis process and run 1.8% agarose gel. The relative apo A1 Milano mRNA levels were quantified against GAPDH, using iO5 Optical System Software analysis (Bio-Rad).

Example 9

ELISA for the Detection of Human ApoA 1 Milano[3]

Serum levels of human apo A1-Milano in the mice with rAAVs were determined by ELISA. ELISA plates were coated with an antihuman apo A1 monoclonal antibody (Calbiochem) at a concentration of 4 ug/ml and incubated at 4° C. overnight. The wells were washed, blocked with 1% fetal bovine serum PBS, and diluted standards (Calbiochem) or serum samples were added to the wells and incubated at 4° C. overnight. After washing, rabbit antihuman apo A1 antibody was added and incubated at room temperature for 2 hours. After washing, a HRP-conjugated goat-antirabbit antibody (Santa Cruz) was added and the color was developed by addition of Substrate Reagent Pack Color Reagent A and B (R&D). Absorbance was measured at 450 nm on a microplate reader. Serum human apo A1-Milano levels were calculated by comparison with the standard curve.

Example 10

Lipoprotein Analysis

Fasting blood samples were collected from mice which carry rAAV by retro-orbital venous plexus puncture using heparinized tubes under isoflurane anesthesia. Total cholesterol was measured using a Cholesterol Calibrators Reagent Enzymatic Kit (sigma).

Example 11

Atherosclerotic Lesion Analysis

Assessment of Atherosclerosis in the Total Aorta:

The extent of the atherosclerotic lesions in the total aorta were quantified after oil red O staining, as described previously [4,5]. Briefly, the thoracic cavity was opened; the aortic arch as well as the aorta were exposed, and were photographed under a dissecting microscope. After capturing the images, most of the vascular tree was dissected intact. The luminal surface was exposed, and then the aortic tissue was fixed with Histo-choice tissue fixative (Amresco, Solon, Ohio). After tissue fixation, the adventitial tissue was removed and aortic tissue was stained for lipids with Oil-Red O. The aortas were pinned to a dark surface, and images were captured by using a Spot digital camera (Diagnostic Instruments, Sterling Heights, Mich.). The extent of the atherosclerotic lesions was quantified using Image-Pro Plus (version 4, Media Cybernetics, Silver Spring, Md.). Lesions were reported as percentage of the total aortic area consisting of thoracic aorta (ending at the final intercostals artery), and abdominal aorta ending at the iliac difurcation.

Assessment of Atherosclerosis in the Innominate Artery:

For innominate artery sections, aortic arch was fixed in 4% paraformaldehyde overnight and then embedded in Optimal Cutting Temperature (OCT). The frozen tissues were serially sectioned into 8-um sections from the aortic arch using a Leica cryostat and kept in a −80° C. freezer for <1 month before use. Tissue was stained with Oil-Red O. The lesion areas were quantified by Image-Pro Plus using the hematoxylin-stained sections (mean of 6 sections per mouse; 5 mice per group).

Assessment of Atherosclerosis in the Aortic Sinus:

To determine cross-sectional lesion area, hearts were embedded in OCT, frozen on dry ice, and then stored at −80° C. until sectioning. Serial sections 8 um thick were collected on slides. Cross sections of the aortic sinus and aortic valve were stained with Oil-Red O. Lesion areas were quantified with Image-Pro Plus by manual tracing of the lesion, which was identified by a combination of lipid staining and histologic morphology.

Immunostaining:

To assess macrophage infiltration into atherosclerotic plaques, macrophage immunoreactivity was detected by immunostaining of frozen sections of innominate and aortic sinus with a 1:100 dilution of rat anti-mouse monocyte/macrophage (MOMA-2) monoclonal antibody (Seiotec). After washing, the sections were incubated with the goat anti-Rat secondary antibodies (Jacksin Immuno Research Lab), and then to apply LSAB streptavidin-HRP 25 min followed by color development. The sections were counterstained with hematoxyli. Photomicroscopy was performed using an Olympus microscope. The percentage of plaque area occupied by MOMA-2 staining, reflecting macrophage immunoreactivity, was calculated from the captured images using the Image-Pro Plus software.

Example 12

Real-Time PCR for Apo A1 Milano Alternatively Activated Macrophage M1 & M2 Phenotype RNA was isolated from peripheral blood mononuclear cell (PBMC), peritoneal macrophages (3% Brewer thioglycollate medium activity) and liver using TRIzol.

The sequences of the primer pairs used in this analysis are indicated in Table 2. The reaction conditions consisted of one 3 min cycle at 94° C., followed by 40 cycles of 94° C. for 10 s, 60° C. for 10 s, and 72° C. for 10 s, which concluded by the melting curve analysis process and run 1.8% agarose gel.

TABLE 2

List of primers

| Gene | For/Rev | Sequences (5' to 3') | SEQ ID NO: |
|---|---|---|---|
| TNF-a | F | TCGTAGCAAACCACCAAGTG | 5 |
|  | R | AGATAGCAAATCGGCTGACG | 6 |
| Il-6 | F | AGACAAAGCCAGAGTCCTTCAG | 7 |
|  | R | TAGGAGAGCATTGGAAATTGG | 8 |

TABLE 2-continued

List of primers

| Gene | For/Rev | Sequences (5' to 3') | SEQ ID NO: |
|---|---|---|---|
| MCP-1 | F | CCCACTCACCTGCTGCTACT | 9 |
|  | R | TCTGGACCCATTCCTTCTTG | 10 |
| Arg-1 | F | CTCCAAGCCAAAGTCCTTAGAG | 11 |
|  | R | AGGAGCTGTCATTAGGGACATC | 12 |
| Ym1 | F | GGGCATACCTTTATCCTGAG | 13 |
|  | R | CCACTGAAGTCATCCATGTC | 14 |
| CD206 | F | GGCAGGATCTTGGCAACCTAGTA | 15 |
|  | R | GTTTGGATCGGCACACAAAGTC | 16 |
| Il-10 | F | AGCTCCAAGACCAAGGTGTC | 17 |
|  | R | CGA GGTTTTCCAAGGAGTTG | 18 |

Example 13

Tests for Circulating Antibody Against Apo A1 Milano (Transgene) by ELISA

Plasma samples of KO apoE/apo A1 mice IV or IM injected with rAAV-apo a1 Milano were tested for the presence of antibodies against apo A1 Milano using an ELISA.

96 wells plates were coated with 1 ug/ml human apo A1 in 0.1 M NaHCO$_3$ pH 9.4, 100 ul/well and then incubated at 4° C. for 12-24 hours. Plates were washed three times with PBS-0.05% Tween-20, 5 min/time.

Plates were blocked with 1% BSA in PBS 200 ul/well at R/T 2 h or 4° C. O/N. Plates were washed three times with PBS-Tween-20, 5 min/time.

Dilute plasma samples (1:16) were applied in duplicate. Dilute Anti-human apo A1 Milano cAb to final concentration of 1 ug/ml as positive control. Negative controls included noninjected and rAAV EGFP injected mice. Plates were incubated 4° C. for 12-24 hours or RT 2 h. Plates were washed three times with PBS-Tween, 5 min/time.

Detection Ab: anti-mouse IgG-HRP was added in a dilution of 1:2000. Plates were incubated for 1 hour at RT. Plates were washed 6 times with PBS-0.05% Tween-20, 5 min/time. Absorbance was measured at 450 nm on a microplate reader. Serum antibody against human apo A1-Milano levels were calculated by comparison with the standard curve.

Example 14

Statistical Evaluation

The Prism 4.0 software (Graphpad, San Diego, Calif.) was used for all calculations. All data are represented as mean SD. Values with $p<0.05$ were considered statistically significant by a one-tailed Student's t test.

Example 15

Expression of Transgene in Circulating Blood

Figure 2:
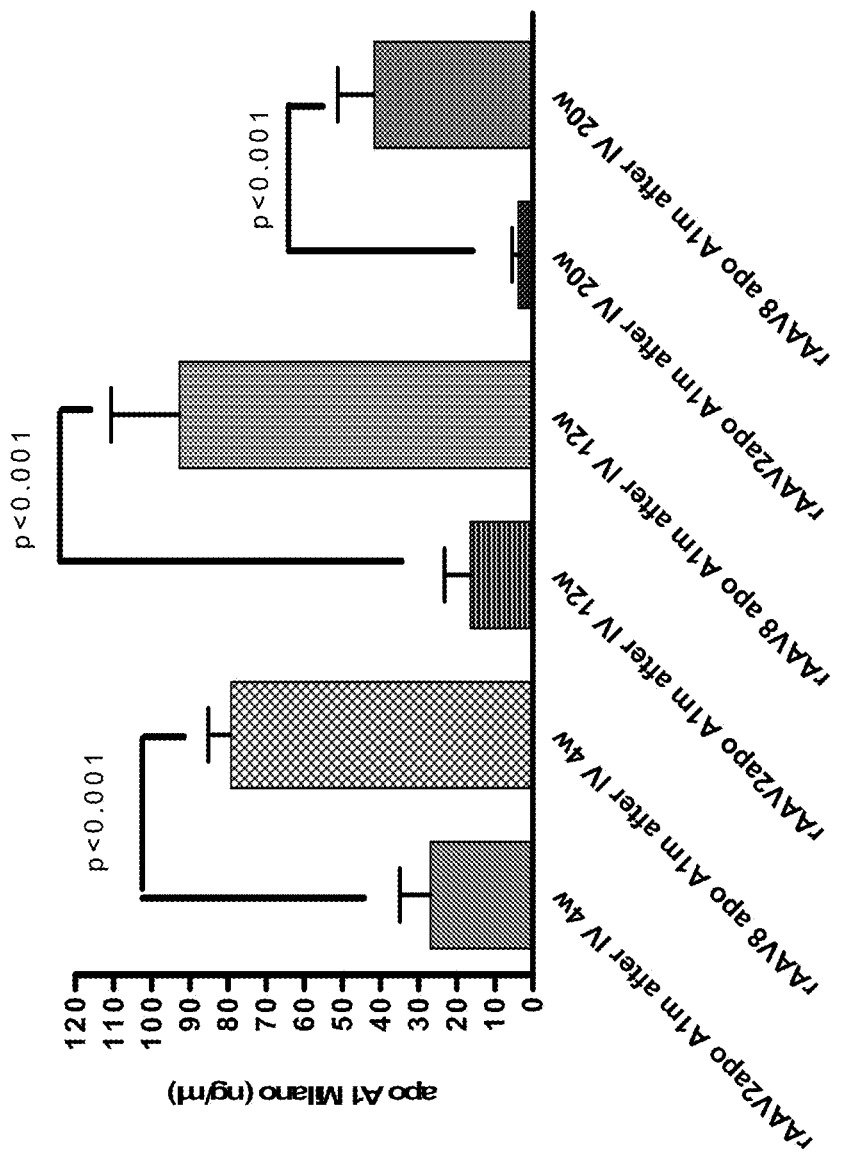
FIG. 2 depicts the comparison of serum levels of apo A1 Milano between mice with rAAV8 and rAAV2 at 4, 12, 24 weeks after IV injection virus in accordance with various embodiments of the present invention. The data represent mean±SD from 12 mice per group. These data show there was statistically significant difference between rAAV8apo A1 Milano and rAAV2 apo A1 Milano. P—Value: rAAV8 apo A1 Milano vs rAAV2 apo A1 Milano at 4, 12 and 20 weeks: P<0.001.
Figure 3:
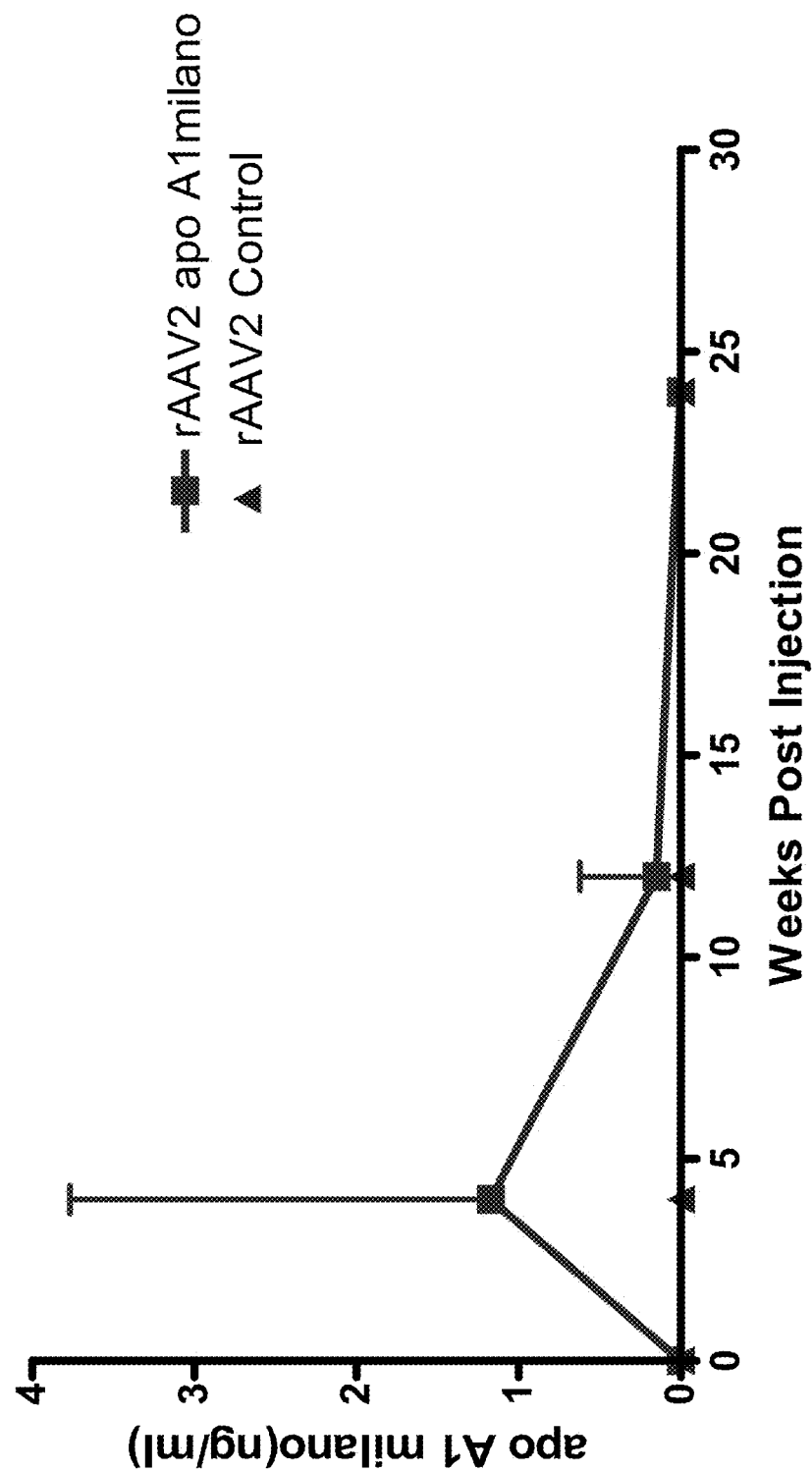
FIG. 3 depicts the expression of apo A1 Milano in the mice with rAAV in accordance with various embodiments of the present invention. Serum levels of apo A1 Milano at 4, 12, 24 weeks after IM injection virus are shown. The data represent mean±SD from 10 mice per group. These data show there was no statistically significant difference between rAAV2 apo A1 Milano and rAAV2 vector control.
Figure 4:
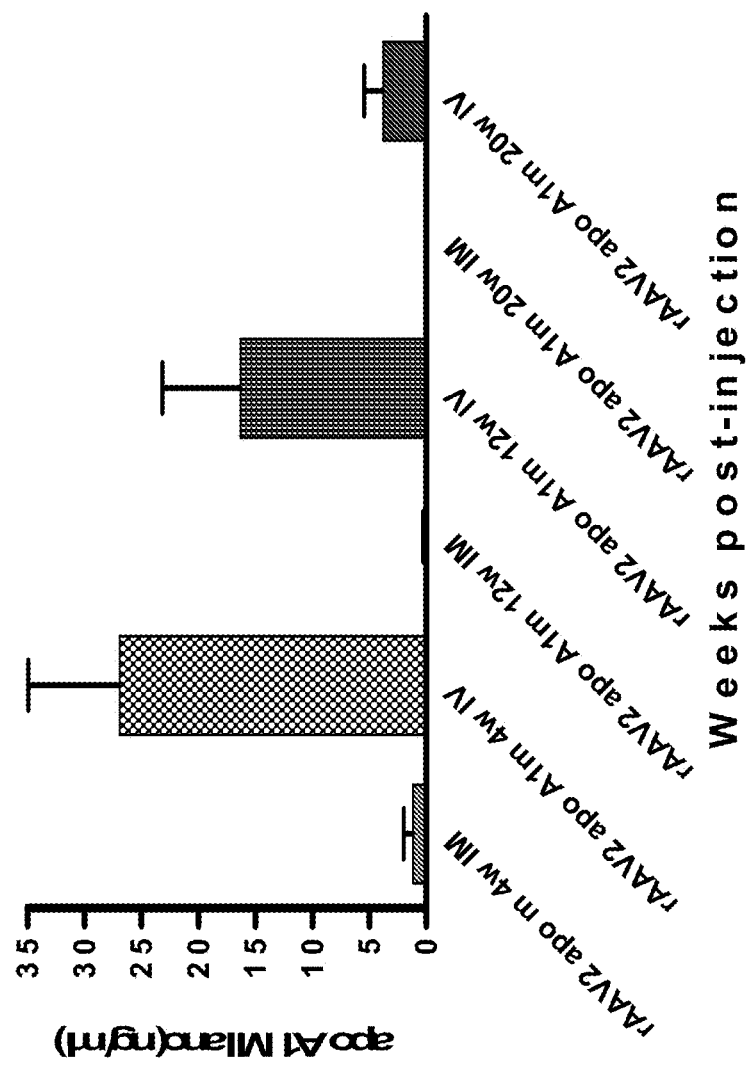
FIG. 4 depicts serum levels of apo A1 Milano in mice from IM and IV delivery with rAAV2 in accordance with various embodiments of the present invention. These data show there was statistically significant difference among AAV2apo A1 Milano IM and AAV2apo A1 Milano IV groups in 4 w, 12 w as well as 20 w (p<0.001).

To compare the expression levels of the transgene in differential groups at designated time points over the course of the stud serum levels of human apo A1 Milano in the gene transfer mice were determined by ELISA. The inventors compared efficacies of 2 different rAAV serotypes, 2 and 8, expressing the human apo A1 Milano in serum in differential groups. They were administered intravenous at single dose (1.2×10e12 of each vector genome/mouse, Table 1, FIG. 1, FIG. 2). As expected, apo A1 Milano was not detected in the serum before injection. Serum apo A1 Milano levels were significantly higher in rAAV8 apo A1 Milano injected mice compared to rAAV2 apo A1 Milano injected mice but in none of the controls. There was significant differences between serotypes, 8 and 2, at 4 weeks (71±31 ng/ml vs. 31±21 ng/ml), at 12 weeks (92±61 ng/ml vs. 30±27 ng/ml), at 24 weeks (45±32 ng/ml vs. 7.6±6 ng/ml) $P<0.001$ all groups. It was found that rAAV8 mediated transgene resulted in apo A1 Milano serum levels that are much higher and for a longer period in vivo than rAAV2. Furthermore, the rAAV2-mediated transgenes expression by intravenous and muscles injection were compared at the same dose. (FIGS. 3, 4) In IM injected mice, apo A1 Milano protein was not detected at week 4, 20 after vector administration, at weeks 12 post injection with maximal expression of 3.6 ng/ml in only two mouse (two-tenth), apo A1 Milano Levels were almost similar in the groups treated with the rAAV2 apo A1 Milano (n=10) compared to vector control (n=10). In contrast, IV delivery resulted in a significant increase of the level of circulating apo A1 Milano protein. There was statistically significant difference among AAV2apo A1 Milano IM and AAV2apo A1 Milano IV groups at designated time point.

Example 16

Tissue Biodistribution of Transgene Expression

Figure 5:
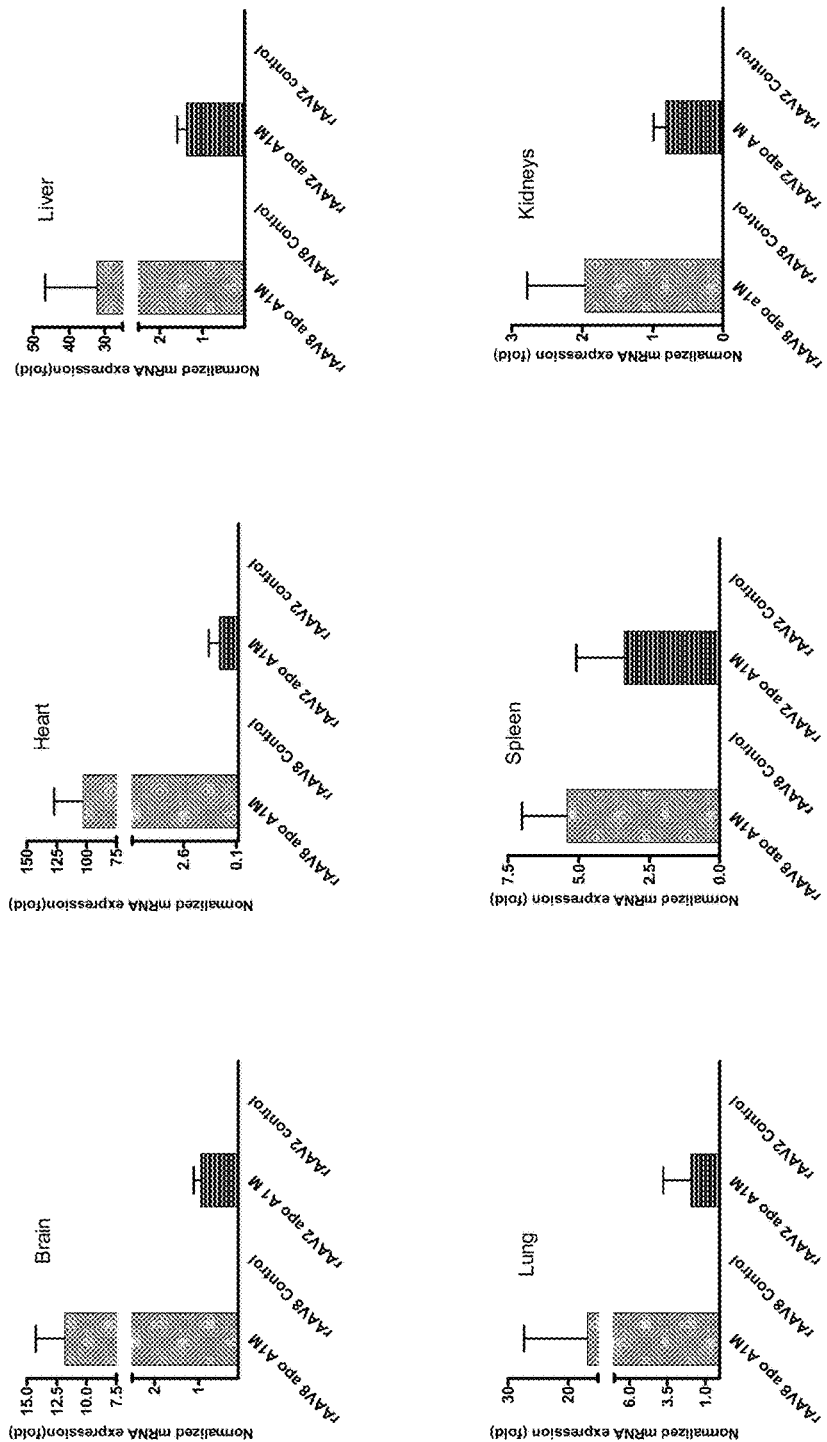
FIG. 5 depicts real-time PCR Quantitative analysis of apo A1 Milano mRNA expression in mice tissues in accordance with various embodiments of the present invention. Values were normalized against GAPDH mRNA. Data showed a significantly higher level of apo A1 Milano. rAAV8 mediated transgene expression compared to rAAV2 in the brain (11.85±2.4 vs 0.95±0, p<0.05), heart (102.3±24.20 vs 0.9±0.5, p<0.001), Liver (32.14±14.56 vs 1.37±0.22, p=0.05), lung (16.49±10.75 vs 1.86±1.8, p=0.25), spleen (5.41±1.59 vs 3.39±1.69, p=0.22) and kidney (1.96±0.8 vs 0.81±0.18, p=0.119).

Because vector doses were identical among all the groups, a comparative analysis of rAAV transducer efficacies was possible in several organs in two serotypes. At 20 weeks after vector administration, a single mouse was killed for each rAAV vector group and total RNA was extracted from brain, lung, heart, liver, spleen, kidney and muscle. The biodistribution of transgene was performed to compare the extent of apo A1 Milano expression in the group treated with rAAV8 (n=3) and rAAV2 (n=3) by real-time PCR. Data showed a significantly higher level of rAAV8 mediated transgene expression in the brain (11.85±2.4 vs 0.95±0, p<0.05), heart (102.3±24.20 vs 0.9±0.5, p<0.001), Liver (32.14±14.56 vs 1.37±0.22, p=0.05), lung (16.49±10.75 vs 1.86±1.8, p=0.25), spleen (5.41±1.59 vs 3.39±1.69, p=0.22) and kidney (1.96±0.8 vs 0.81±0.18, p=0.119) with rAAV8 apo A1 Milano compared to rAAV2 apo A1 Milano (FIG. 5). This indicated that rAAV8 treatment elicited higher widespread gene transfer in differential tissues than rAAV2. The biodistribution of the AAV8 serotype was interesting in that it demonstrated a wide tissue distribution. Also rAAV8 mediated more efficient apo A1 Milano expression than rAAV2 with same titer of viral vector.

Example 17

Effect on Aortic Atherosclerosis

Figure 6A:
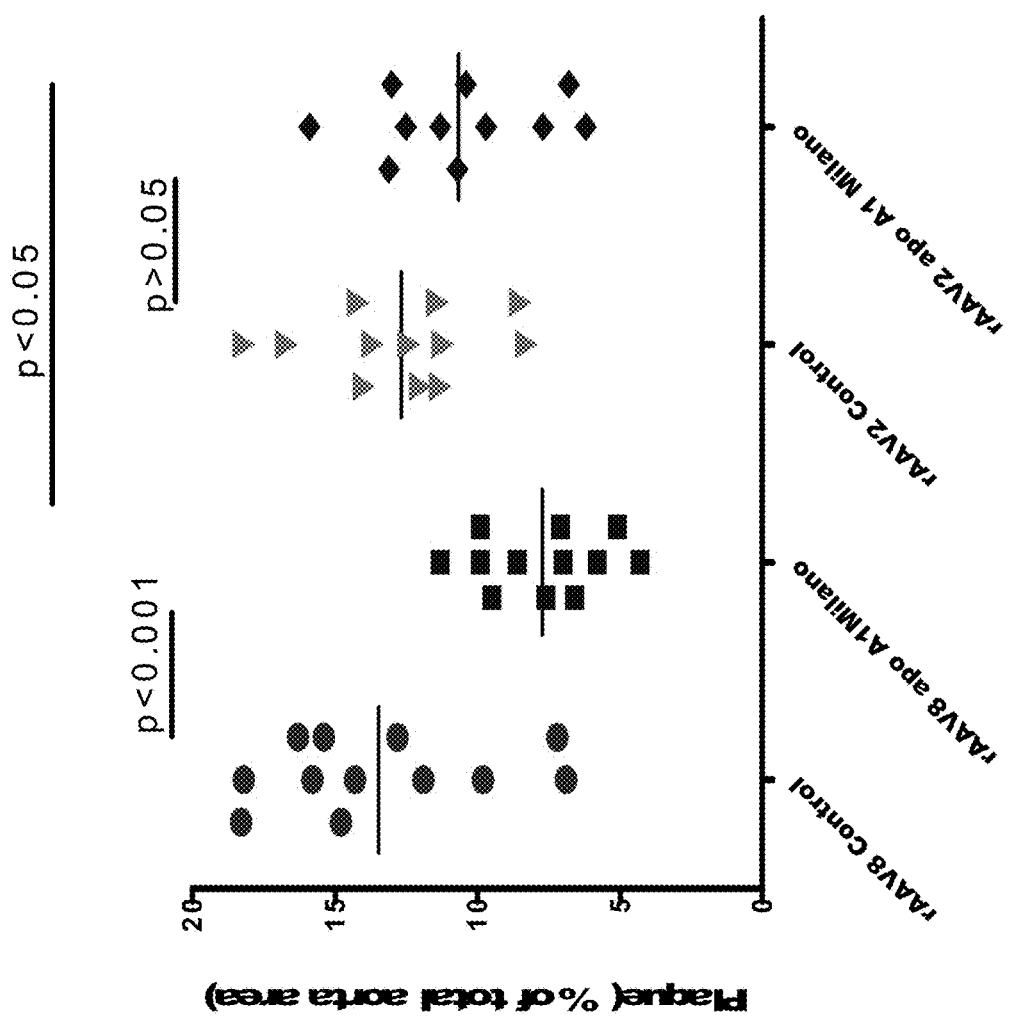
FIG. 6A shows that the mean aortic lesion areas were reduced by 42% in rAAV8 apo A1 Milano vector compared to control vector (7.7±0.6% vs. 13.5±1.1%, p=0.0002) in accordance with various embodiments of the present invention. However, the differences in the mean lesional area between recipient of rAAV2 apo A1 Milano vector and control vector was insignificant (p=0.1193) compared to rAAV2 apo A1 Milano vector, rAAV8 apo A1 Milano vector reduced lesion areas by 27% (p=0.006).
Figure 6B:
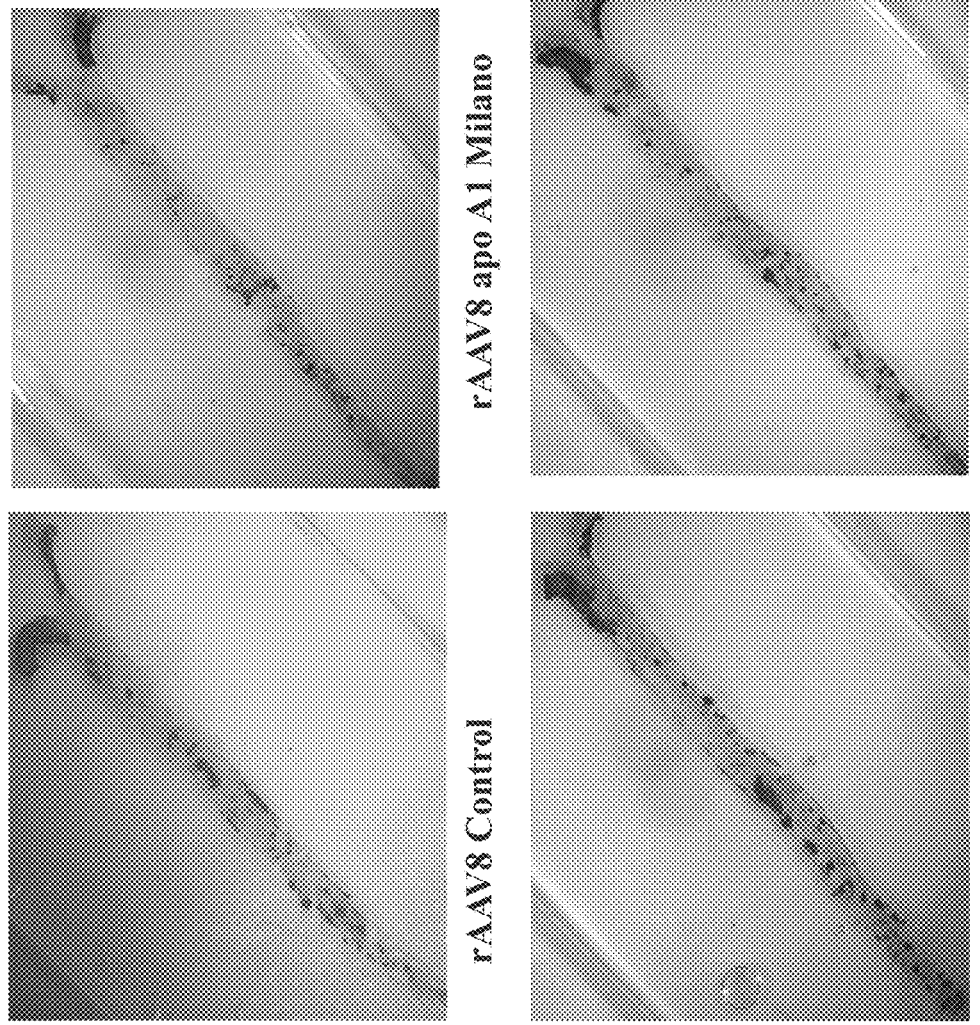
FIG. 6B depicts the extent of the atherosclerotic lesions in the total aorta were quantified after Oil Red O staining in accordance with various embodiments of the present invention.
Figure 7:
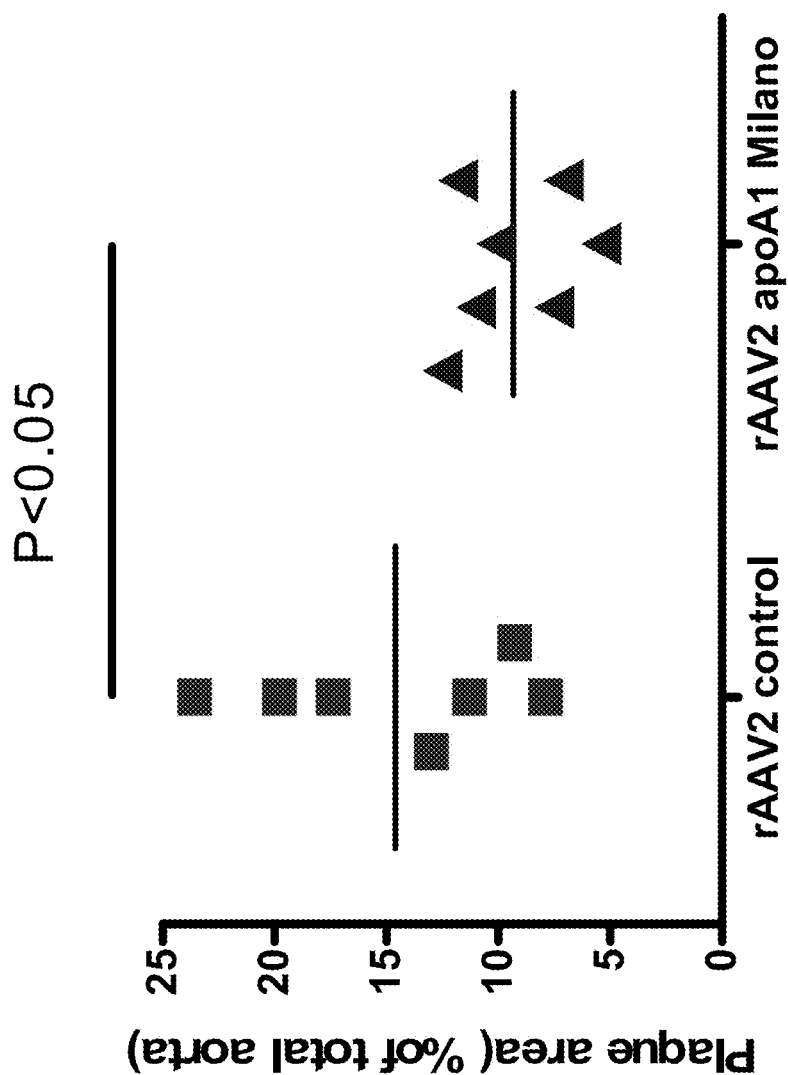
FIG. 7 shows that in the intramuscular group, the differences in the mean lesional area between recipient of rAAV2 apo A1 Milano vector and control vector was significant (9.34±1.01 vs 14.6±2.2, N=7), reflecting a 36% reduction (p=0.04) in accordance with various embodiments of the present invention.

Atherosclerosis progression in the total aorta was determined by Oil-Red O staining. The mean lesion area of total aorta in mice treated with rAAV8 apo A1 Milano by IV was 7.7±0.6% (n=11), versus 13.5±1.1% (n=12) in mice receiving the rAAV8 control vector, reflecting a 42% reduction (p=0.0002) (FIG. 6 A, B). In contrast, the mean lesion area in the mice treated with rAAV2 apo A1 Milano by IV was 10.66±0.89 (n=11), versus 12.66±0.84 (n=12) in mice receiving the rAAV2 control vector, reflecting a 25% reduction (p=0.119). Aortic atherosclerosis was significantly less in rAAV8 apo A1 Milano treated mice than rAAV2 apo A1 Milano treated mice reflecting a 27% reduction (p=0.006). Mean lesion areas were highly correlated with plasma levels of human apo A1 Milano in mice which were treated with rAAV8. However, in rAAV2 intramuscular group the mean lesional area in total aorta recipient of rAAV2 apo A1 Milano vector was significantly lower than the control vector (9.34±1.01 vs 14.6±2.2, N=7), reflecting a 36% reduction (p=0.04, FIG. 7).

Example 18

Effect on Innominate Artery and Aortic Sinus Atherosclerosis

Figure 8:
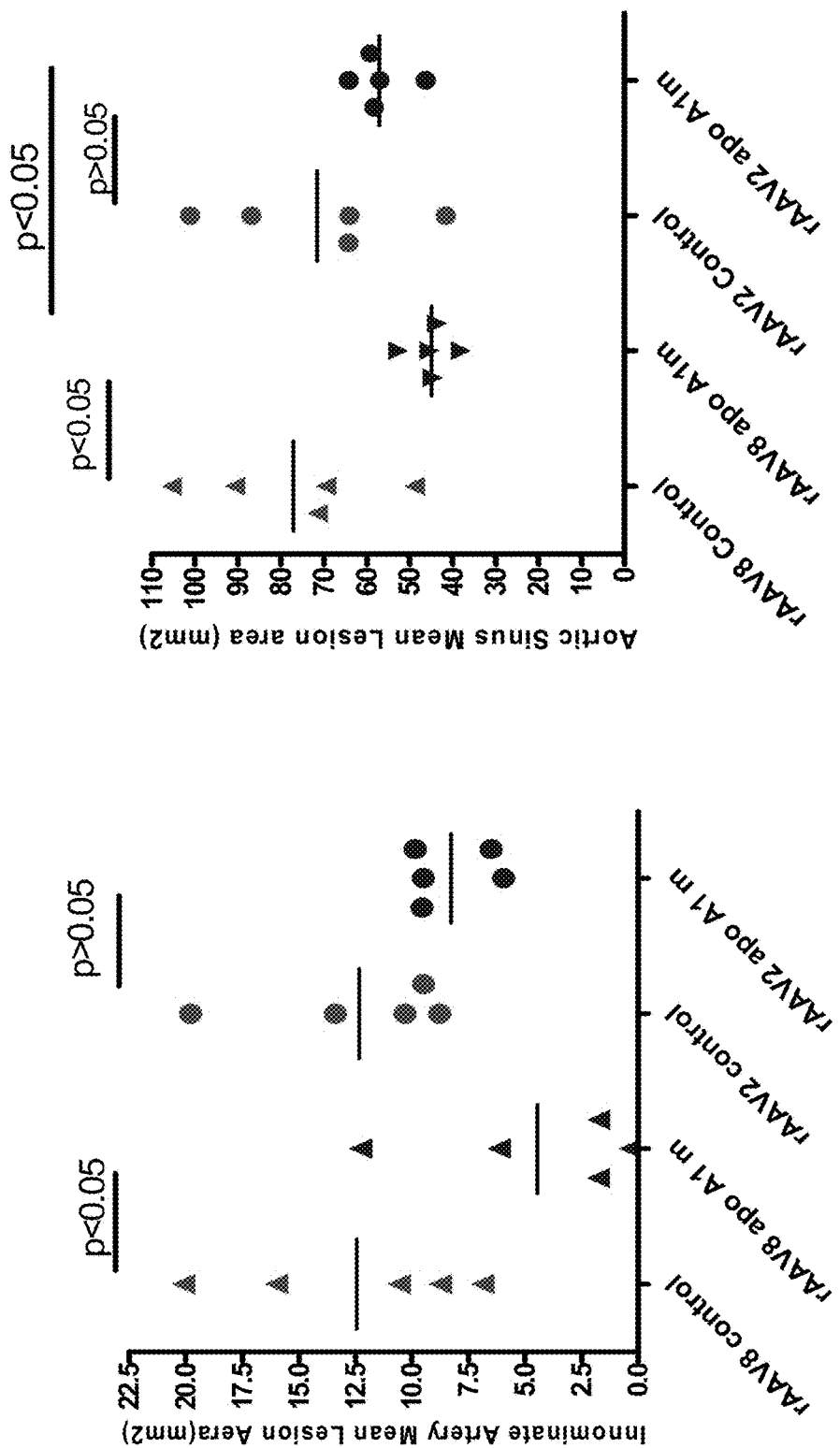
FIG. 8 depicts the average percent lesion areas in accordance with various embodiments of the present invention in innominate artery (left panel) and aortic sinus (right panel) in rAAV8 vector control, rAAV8 apo A1 Milano and rAAV2 vector control; rAAV2 apo A1 Milano are shown. Mice treated with rAAV8 apo A1 Milano had significantly smaller lesion areas compared with vector control mice (P<0.05).

The mean innominate artery lesion area (mm$^2$) in mice treated with rAAV8 apo A1 Milano was 4.45±2.2, versus 12.44±2.4 in mice receiving the control vector, reflecting a 62% reduction (p=0.02) (FIG. 8 a); in contrast, the mean lesion area in mice treated with rAAV2 apo A1 Milano was 8.3±0.8, versus 12.34±2.0 in mice receiving the control vector, reflecting a 33% reduction (P=0.05). Compared to rAAV2 apo A1 Milano vector, rAAV8 apo A1 Milano vector reduced lesion areas by 27% (p=0.07). The mean aortic sinus artery lesion area (mm$^2$) in mice treated with rAAV8 apo A1 Milano was 44.84±2.3, versus 77.13±9.6 in mice receiving the control vector, reflecting a 41% reduction (p=0.01) (FIG. 8 b); in contrast, the mean lesion area in mice treated with rAAV2 apo A1 Milano was 57.0±3.0, versus 71.6±10.3 in mice receiving the control vector, reflecting a 22% reduction (P=0.05). Compared to rAAV2apo A1 Milano vector, rAAV8 apo A1 Milano vector reduced lesion areas significantly by 21% (p=0.006).

Example 19

Lipid Content in Innominate Artery and Aortic Sinus Atheromatous Plaque

Figure 9:
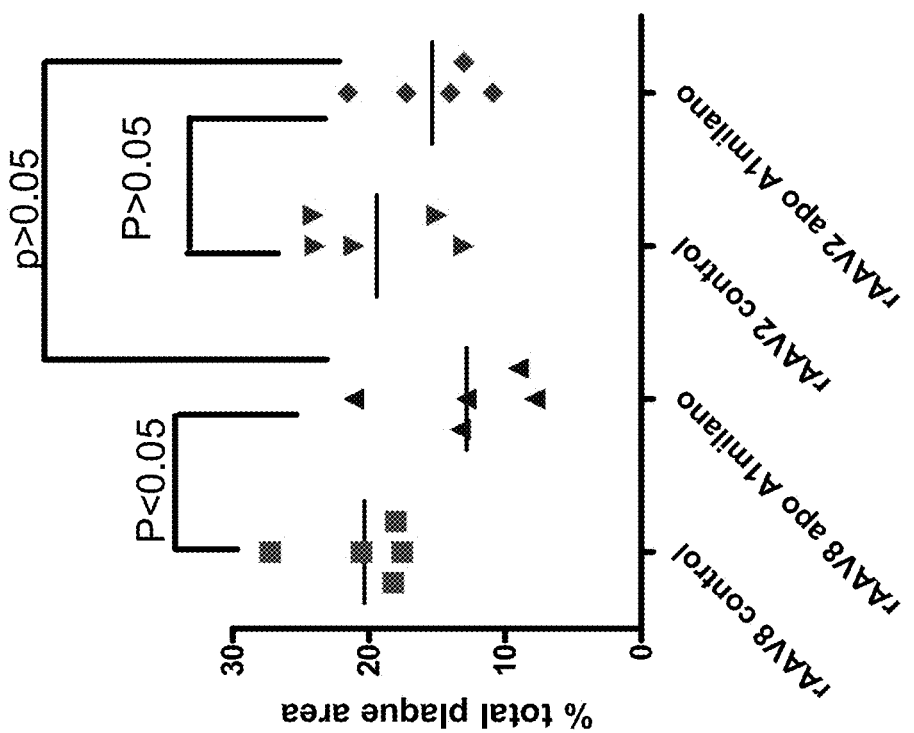
FIG. 9 depicts the lipid content determined in innominate artery and aortic sinus atheromatous plaque by Oil-Red O staining in accordance with various embodiments of the present invention. The lipid content was significantly lower in mice treated with rAAV8 apo A1 Milano compared with vector control or rAAV2 apo A1 Milano.
Figure 9:
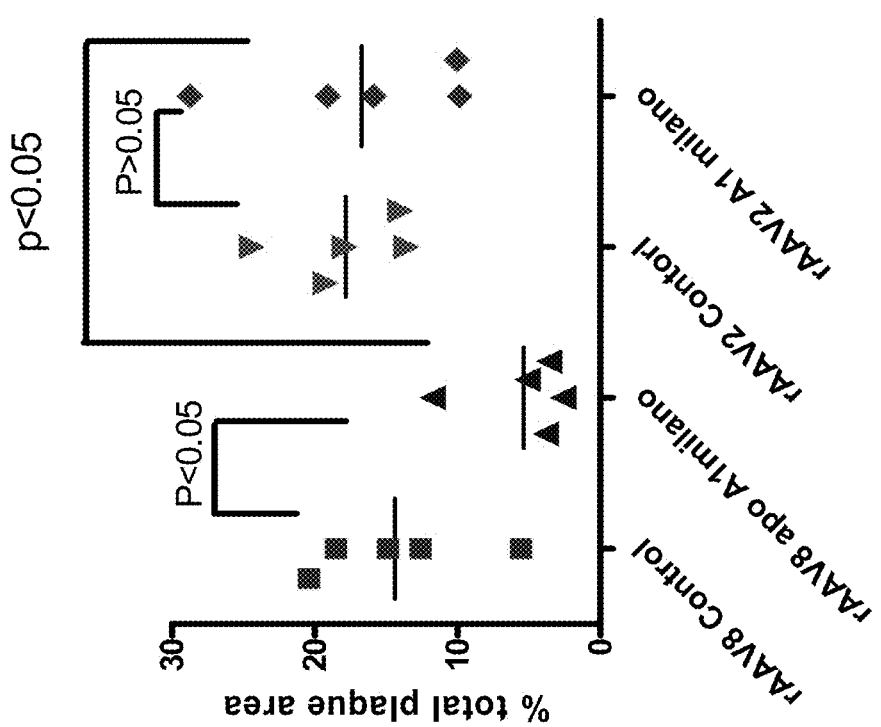

The lipid content was determined by Oil-Red O staining. The lipid content in innominate plaque in mice treated with rAAV8 apo A1 Milano was 5.4±1.6%, versus 14.41±2.6% in mice receiving the control vector, reflecting a 62% reduction (p=0.02) (FIG. 9 a). In contrast, the lipid content in mice treated with rAAV2 apo A1 Milano was 16.73±3.5, versus 17.84±2.3 mice receiving the control vector, reflecting a 6% reduction (P=0.78). The lipid content in plaque area was significantly less in mice receiving rAAV8 apo A1 Milano vector (p=0.009) compared to rAAV2apo A1 Milano vector. Similarly, the lipid content in aortic sinus plaque in mice treated with rAAV8 apo A1 Milano was 12.84±2.3%, versus 20.33±1.8% in mice receiving the control vector, reflecting a 58% reduction (p=0.03) (FIG. 9b). In contrast, the lipid content in mice treated with rAAV2 apo A1 Milano was 15.37±1.6%, versus 19.45±2.3% in mice receiving the control vector, reflecting a 21% reduction (P=0.204). The lipid content in plaque area was lower in mice receiving rAAV8 apo A1 Milano vector than rAAV2apo A1 Milano vector, reflecting a 16% reduction (p=0.2).

Example 20

Macrophage Content in Innominate Artery and Aortic Sinus Atheromatous Plaque

Figure 10B:
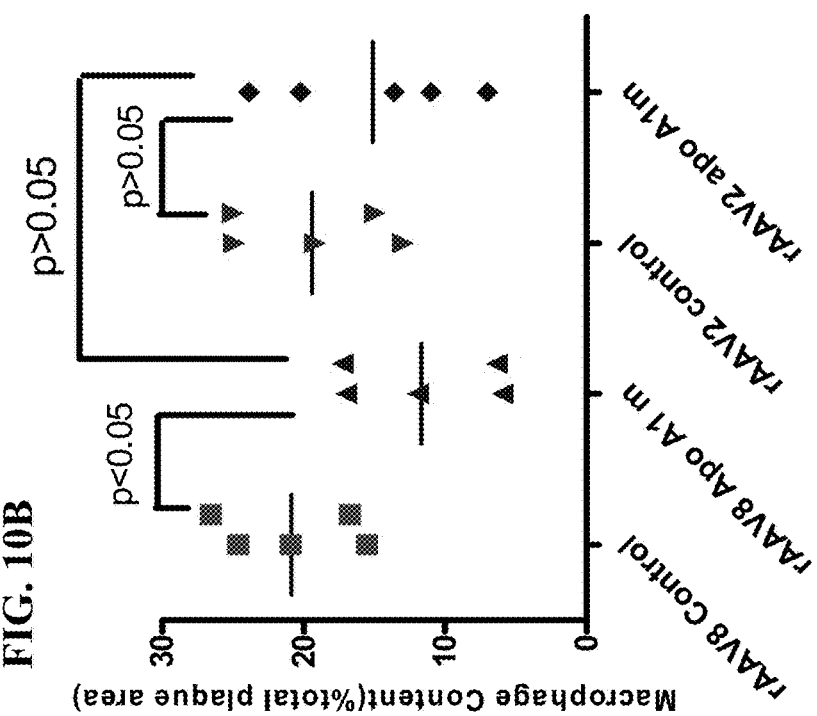
FIG. 10A-10B depicts quantitative data of macrophage immunoreactivity in the innominate artery lesions (FIG. 10A) and aotic sinus lesions (FIG. 10 B) in accordance with various embodiments of the present invention. The macrophage immunoreactive area was significantly lower in mice treated with rAAV8 apo A1 Milano compared with vector control or rAAV2 apo A1 Milano.
Figure 10A:
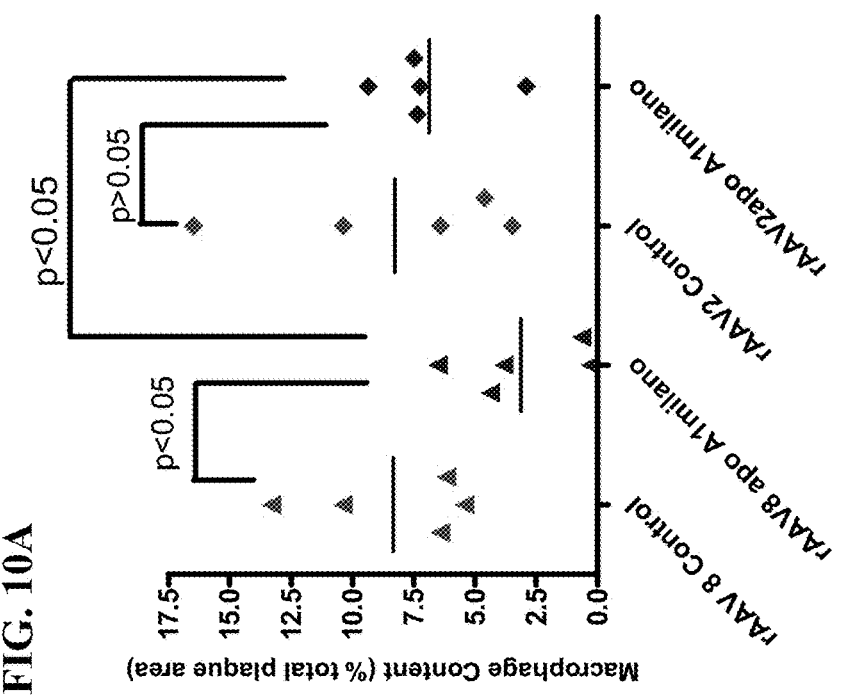
Figure 10C:
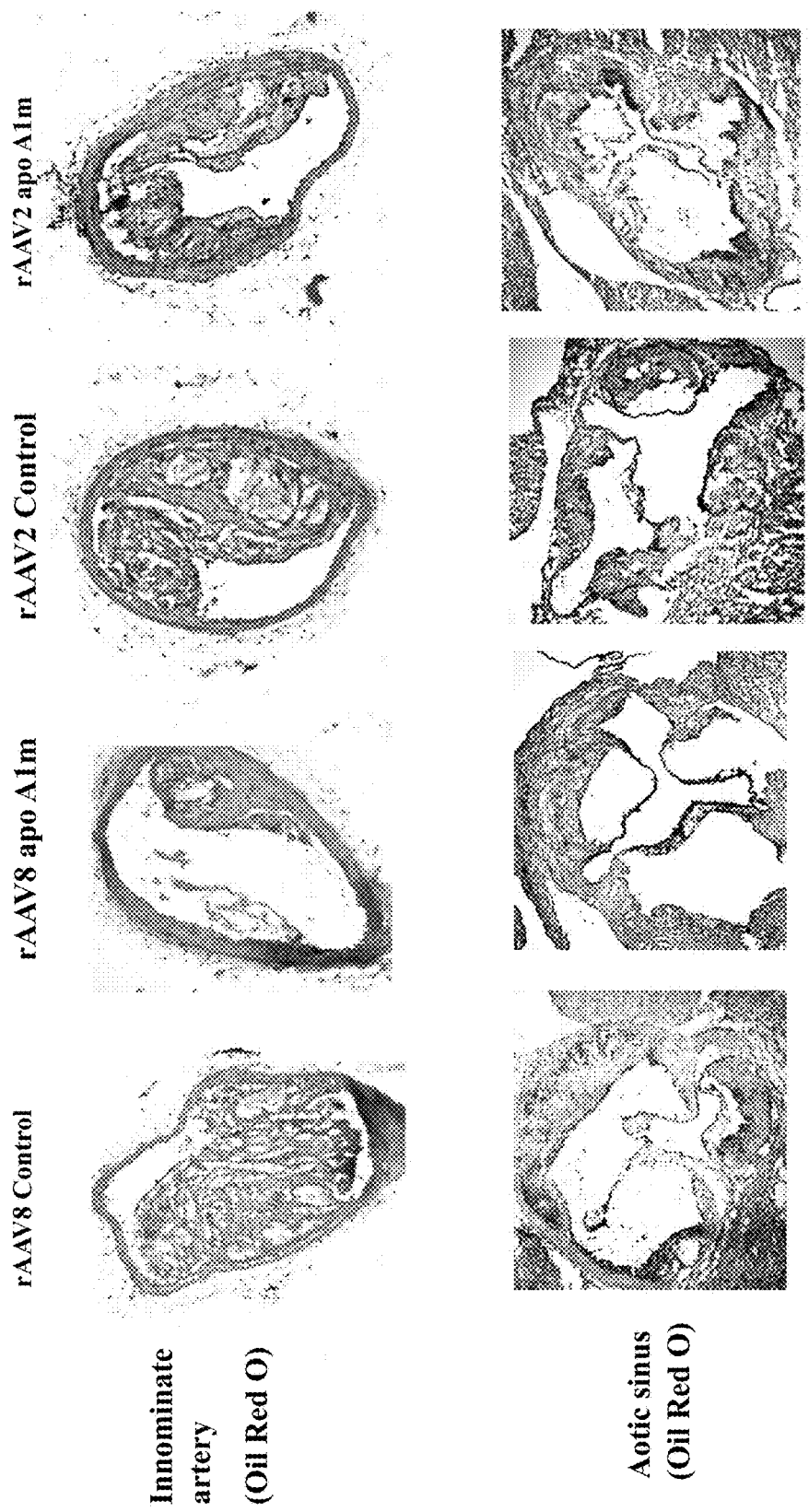
FIG. 10C depicts use of immunostaining to assess macrophage infiltration into atherosclerotic plaques.

The reduction in lesion size was associated with reduced macrophage immunoreactivity. The macrophage content in innominate plaque in mice treated with rAAV8 apo A1 Milano was reduced by 62% compared with mice receiving the control vector (3.12±1.2%, versus 8.3±1.5% (p=0.02)) (FIG. 10 A, C). In contrast, the macrophage content in mice treated with rAAV2 apo A1 Milano was 6.86±1.1%, versus 8.26±2.37% in mice receiving the control vector, reflecting a 16% reduction (P=0.78). The macrophage content in innominate plaque area was significantly less in mice receiving rAAV8 apo A1 Milano vector compared to rAAV2apo A1 Milano vector (p=0.02). Similarly, the macrophage content in aortic sinus plaque in mice treated with rAAV8 apo A1 Milano was 11.7±2.5%, versus 20.9±2.1% in mice receiving the control vector, reflecting a 44% reduction (p=0.01) (FIG. 10 B, C). In contrast, the macrophage content in mice treated with rAAV2 apo A1 Milano was 15.14±3.1%, versus 19.43±2.5% in mice receiving the control vector, reflecting a 22% reduction (P=0.2). The macrophage content in plaque area was less in mice receiving rAAV8 apo A1 Milano vector than rAAV2apo A1 Milano vector, reflecting a 22% reduction (p=0.203).

Example 21

Apo A1 Milano Induces a Phenotypic Switch of Macrophages from M1 to M2

Figure 11:
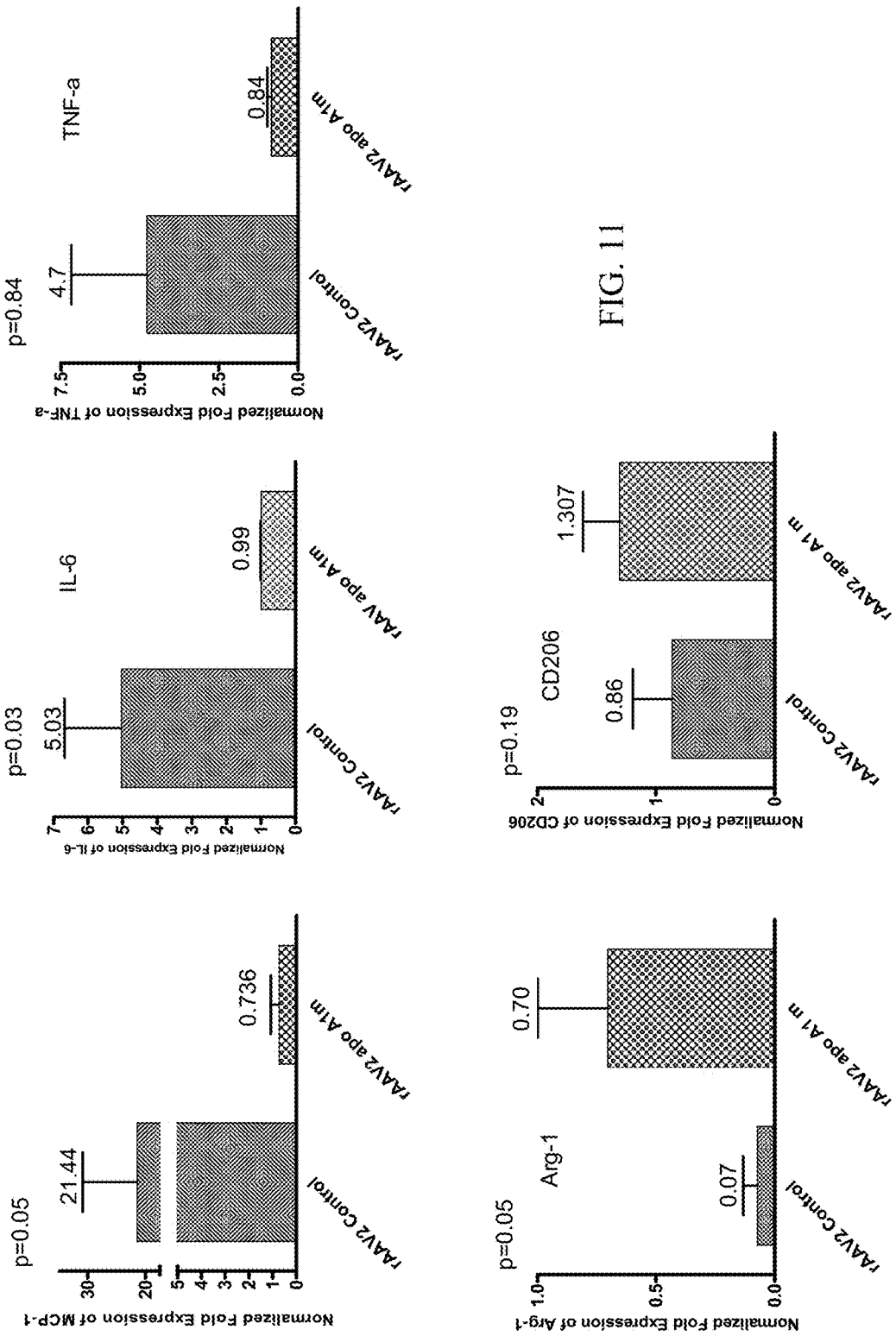
FIG. 11 shows that M1 and M2 macrophage marker are expressed in monocyte in mice treated with rAAV2 by IM (n=4) in accordance with various embodiments of the present invention. mRNA levels were measured by real-time PCR. Numbers indicate the average of the group and P value (unpaired Student's t test).
Figure 12:
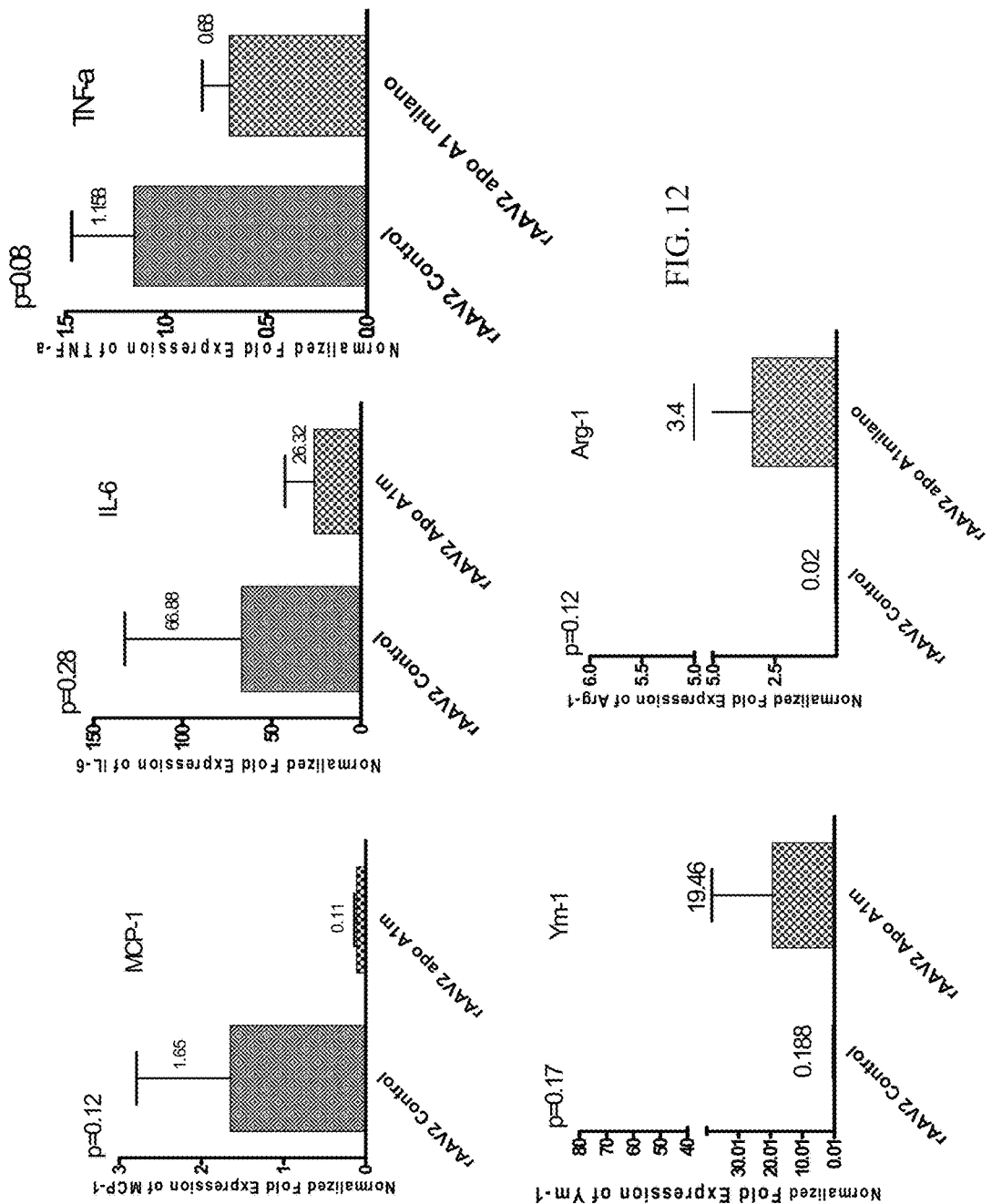
FIG. 12 shows that M1 and M2 macrophage marker are expressed in peritoneal macrophage in mice treated with rAAV2 by IM (n=4) in accordance with various embodiments of the present invention. mRNA levels were measured by real-time PCR. Numbers indicate the average of the group and P value. (unpaired Student's t test).
Figure 13:
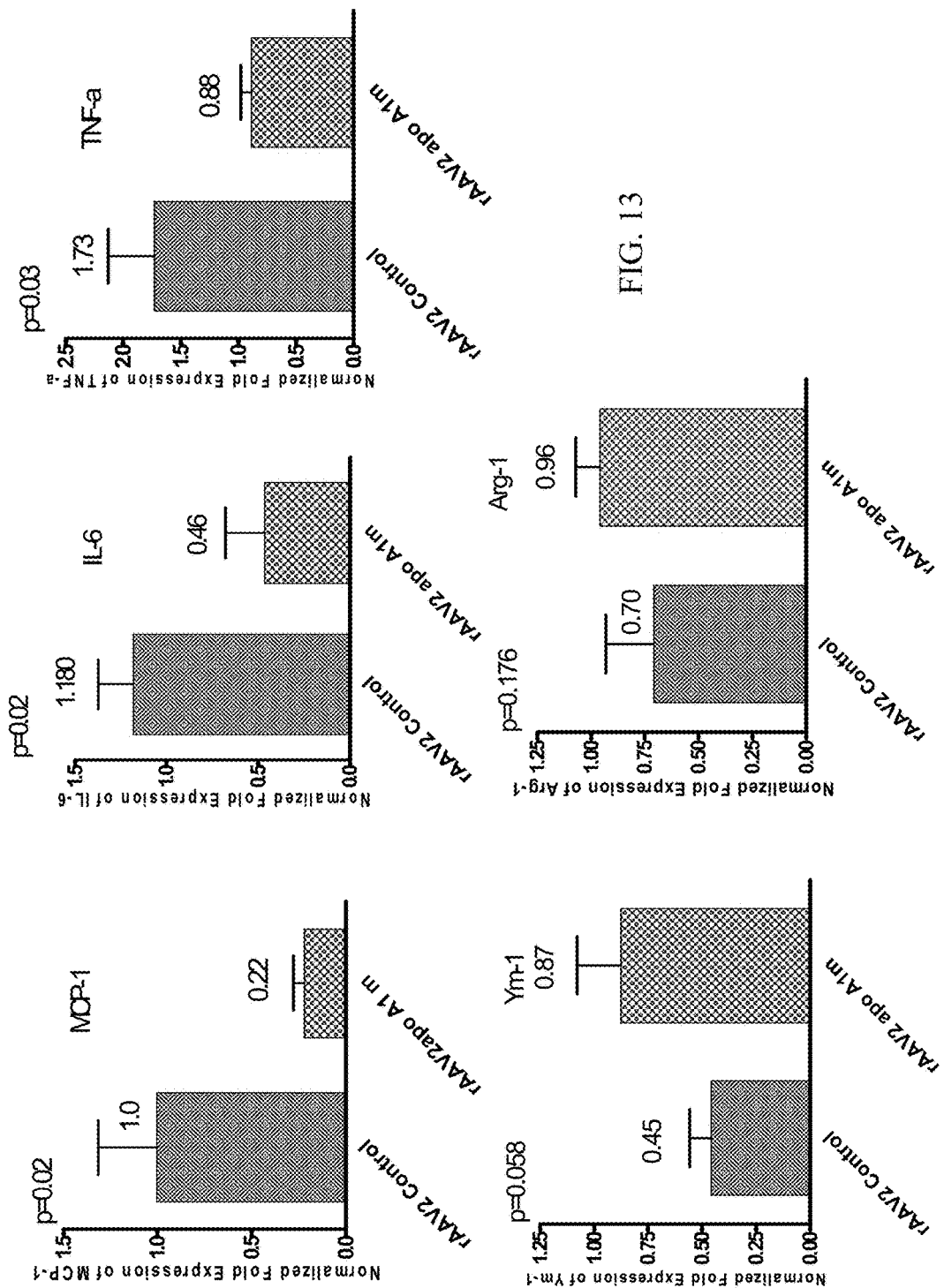
FIG. 13 shows that M1 and M2 macrophage marker are expressed in liver in mice treated with rAAV2 by IM (n=4) in accordance with various embodiments of the present invention. mRNA levels were measured by real-time PCR. Numbers indicate the average of the group and p value (unpaired Student's t test).
Figure 14:
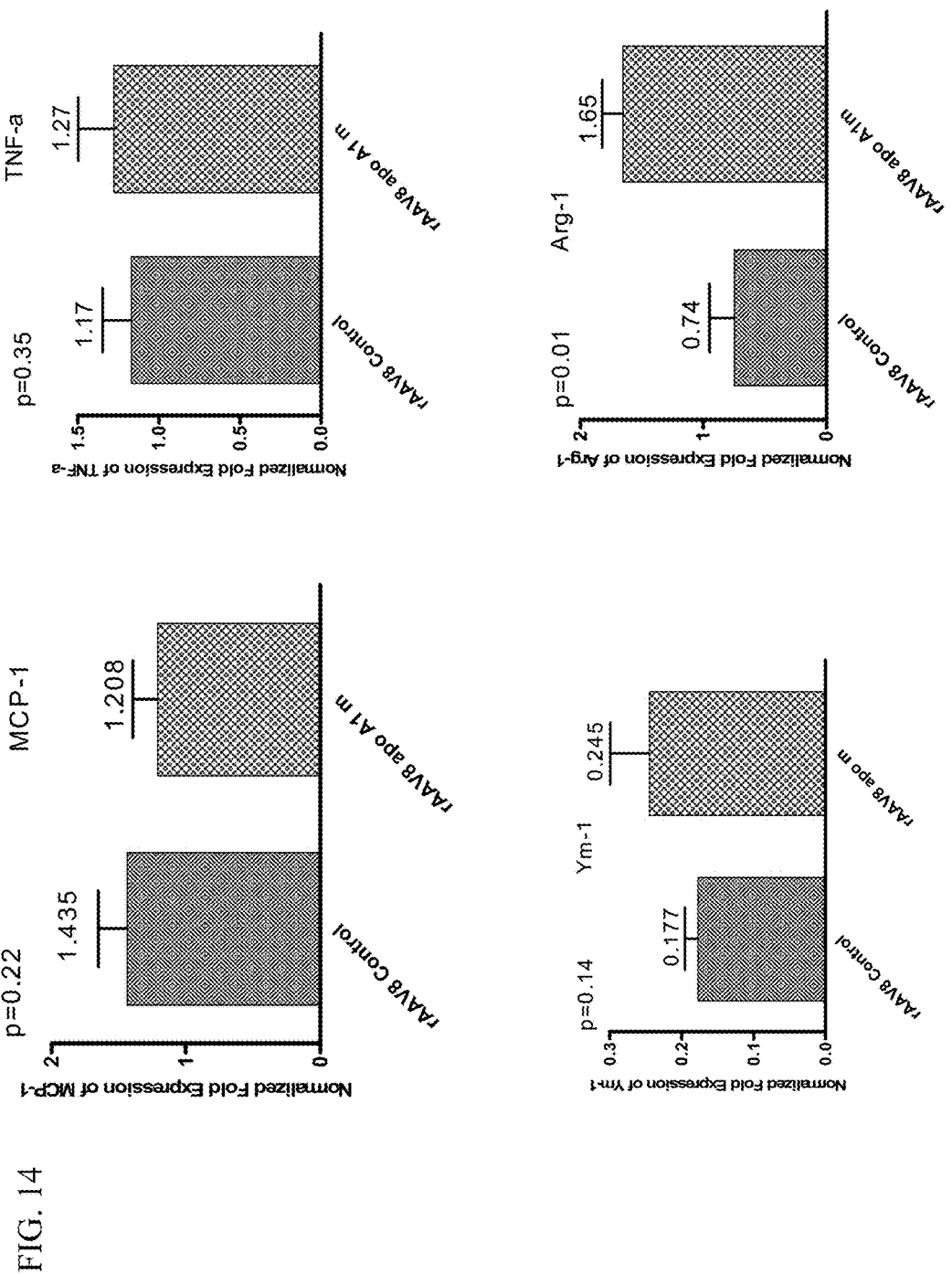
FIG. 14 shows that M1 and M2 macrophage marker are expressed in liver in mice treated with rAAV8 by IV (n=4) in accordance with various embodiments of the present invention. mRNA levels were measured by real-time PCR. Numbers indicate the average of the group and P value (unpaired Student's t test).
Figure 15:
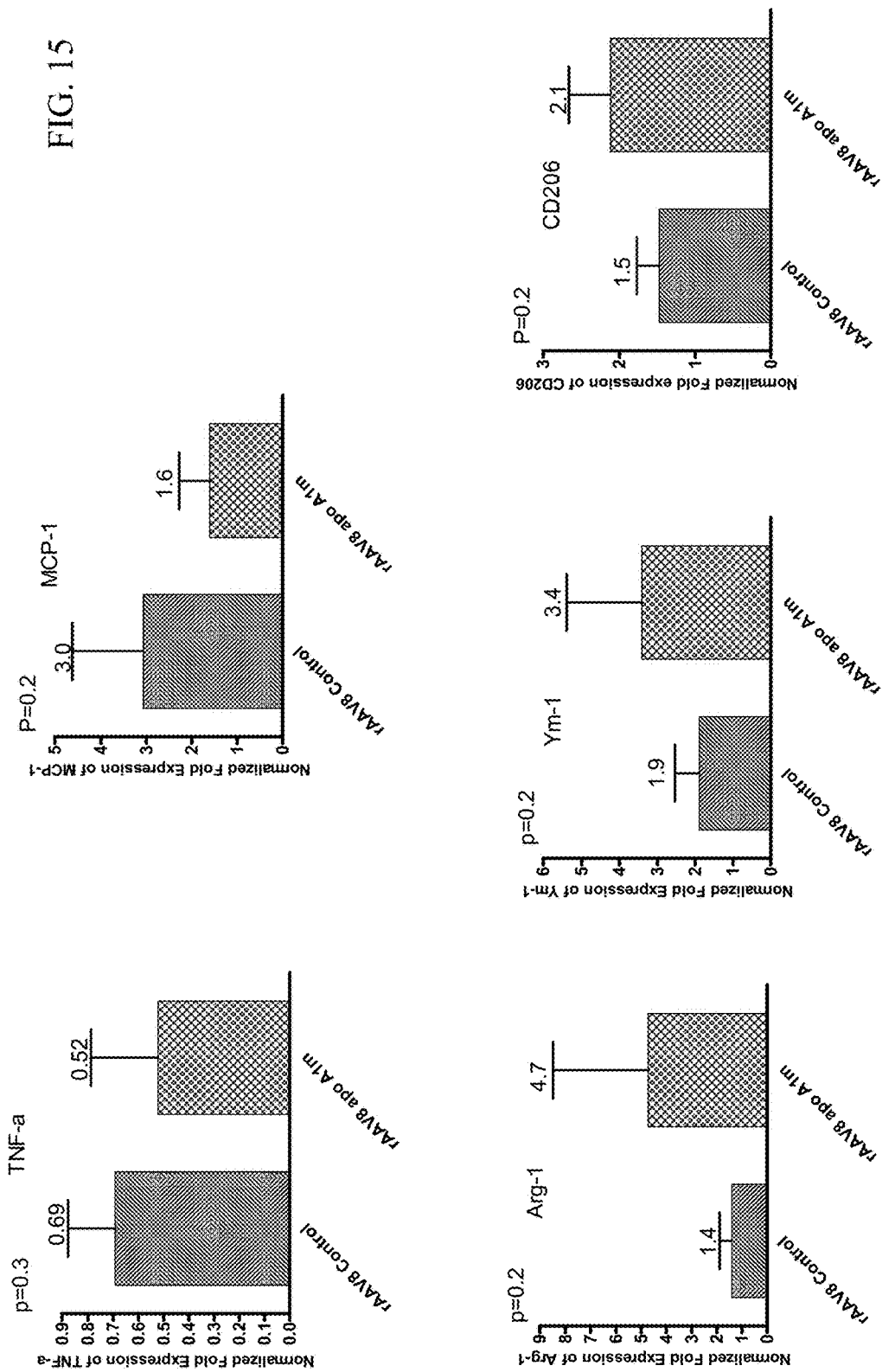
FIG. 15 shows that M1 and M2 Macrophage number are expressed in monocytes in mice treated with rAAV8 (n=4), mRNA levels were measured by Real-time PCR. Numbers indicate the average of the group and p value (unpaired Student's t test).

Previous studies have identified that activated macrophages acquire a proinflammatory (M1) or anti-inflammatory (M2) phenotype that influences atherosclerosis. In order to identify the mechanism of apo A1 Milano that inhibits atherosclerosis progression in mouse models, the inventors observed whether anti-inflammatory effects of apo A1 Milano in apoE/apo A1 Milano deficient mice by focusing on the expression proinflammatory M1 type monocyte/macrophage marker and anti-inflammatory M2 type monocyte/macrophage marker. To test whether the cells bear less characteristics of M1 and more characteristics of M2 cells the inventors subjected monocyte, macrophage as well as liver from mice treated with rAAV apo A1 Milano to real time PCR analysis using primer pairs (Table 2) for molecules that have been used classify monocytes/macrophages into the M1 and M2 subtypes [6, 7]. As shown in FIG. 11, the proinflammatory M1 marker MCP-1, IL-6 as well as TNF-a were down-regulated, however anti-inflammatory M2 marker Arg-1 and CD206 up-regulated in primary murine monocytes in mice treated with rAAV2 apo A1 Milano by IM compared to vector control (n=4). Such anti-inflammatory phenomenon were also evident in peritoneal macrophage and liver, it was found that mice treated with apo A1 Milano markedly reduced M1 marker MCP-1, IL-6 and TNF-a mRNA expression and modestly increased M2 Marker Arg-1 and YM1 mRNA expression in primary macrophages and Liver compared to vector control (n=4) (FIGS. 12, 13, 14, 15). Mouse GAPDH was measured as a housekeeping gene for normalization purposes. These findings demonstrate an important role for apo A1 Milano in the regulation of macrophage phenotypic switching in atherosclerosis.

REFERENCES

1. Behrooz G. Sharifi, Kaijin Wu, Lai Wang, et al. AAV serotype-dependent apolipoprotein A-1 $_{Milano}$ gene expression. Atherosclerosis 2005; 181: 261-269
2. S Zolotukhin, B J Byrne, N Muzyczka, et al. Recombinant adeno-associated virus purification using novel methods improves infectious titer and yield. Gene Therapy 1999; 6:973-985

3. Lai Wang, Behrooz G. Sharifi, Prediman K. Shah, et al. Bone marrow Transplantation Shows Superior Atheroprotective Effects of Gene Therapy With Apolipoprotien A-1 Milano Compared with Wild-Type Apolipoprotein A-1 in Hyperlipidemic Mice. JACC 2006; 48:1459-1468
4. Shah P K, Nilsson J, Kaul S, et al. Effects of recombinant apolipoprotein A-1 (Milano) on aortic atherosclerosis in apolipoprotein E-deficient mice. Circulation 1998; 97:780-5.
5. Shah P K, Yano J, Reyes O et al. High-dose recombinant apolipoprotein A-1 Milano mobilizes tissue cholesterol and rapidly reduces plaque lipid and macrophage content in apolipoprotein E-deficient mice; potential implications for acute plaque stabilization. Circulation 0.2001; 103: 3045-50.
6. David M. Mosser, Justin P. Edwards. Exploring the full spectrum of macrophage activation. Nature reviews immunology 2008; 8:958-969
7 Jamila Khallou-Laschet, Aditi Varthaman, Giulia Fornasa et al. Macrophage Plasticity in Experimental Atherosclerosis. PloS ONE 2010; 5(1):1-10

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of reducing plaque lipid content or plaque macrophage content in an aortic sinus, an innominate artery, or both, and optionally monitoring monocyte or macrophage phenotypic switching, in a subject in need of changing the phenotype of a monocyte or macrophage from a proinflammatory M1 phenotype to an anti-inflammatory M2 phenotype, comprising:

administering to the subject an effective amount of a composition comprising serotype 8 recombinant adeno-associated virus (rAAV8) to change the phenotype of the monocyte or macrophage from the proinflammatory M1 phenotype to the anti-inflammatory M2 phenotype, said rAAV8 further comprises an exogenous gene encoding apolipoprotein A-I Milano (ApoA-I Milano), wherein the plaque lipid content or the plaque macrophage content in the aortic sinus, the innominate artery, or both is reduced, and wherein the serum level of ApoA-I Milano protein in the subject is 102 ng/mL or less at four weeks after administration of the rAAV8 by intravenous injection.

2. The method of claim 1, comprising monitoring the monocyte or macrophage phenotypic switching in the subject comprising:

measuring the expression levels of monocyte chemoattractant protein-1 (MCP-1), interleukin 6 (IL-6), tumor necrosis factor alpha (TNF-a), arginase 1 (Arg-1), beta-N-acetylhexosaminidase Ym-1 and cluster of differentiation 206 (CD206) to monitor monocyte or macrophage phenotypic switching in the subject in need thereof; and determining the presence of a phenotypic switch from a proinflammatory M1 macrophage to an anti-inflammatory M2 macrophage when MCP-1, IL-6, TNF-a or a combination thereof is down-regulated, and/or Arg-1, Ym-1, CD206 or a combination thereof is up-regulated, or determining the absence of a phenotypic switch from the proinflammatory M1 macrophage to the anti-inflammatory M2 macrophage when MCP-1, IL-6, TNF-a or a combination thereof is not down-regulated, and/or Arg-1, Ym-1, CD206 or a combination thereof is not up-regulated, or determining the presence of a phenotypic switch from an anti-inflammatory M2 macrophage to a proinflammatory M1 macrophage when MCP-1, IL-6, TNF or a combination thereof is up-regulated, and/or Arg-1, CD206 or a combination thereof is down-regulated, or determining the presence of a phenotypic switch from a proinflammatory M1 macrophage to an anti-inflammatory M2 macrophage when MCP-1, IL-6, TNF-a or a combination thereof is down-regulated, and/or when Arg-1, Ym-1, CD206 or a combination thereof is not up-regulated.

3. The method of claim 1, comprising reducing the plaque lipid content in an aortic sinus, an innominate artery, or both.

4. The method of claim 1, comprising reducing the plaque macrophage content in an aortic sinus, an innominate artery or both.

5. The method of claim 1, wherein the subject is a human.

* * * * *

```
                        SEQUENCE LISTING

<160> NUMBER OF SEQ ID NOS: 18

<210> SEQ ID NO 1
<211> LENGTH: 20
<212> TYPE: DNA
<213> ORGANISM: Homo sapiens

<400> SEQUENCE: 1
tggatgtgct caaagacagc                                                    20

<210> SEQ ID NO 2
<211> LENGTH: 20
<212> TYPE: DNA
<213> ORGANISM: Homo sapiens

<400> SEQUENCE: 2
aggccctctg tctcctttc                                                     20

<210> SEQ ID NO 3
<211> LENGTH: 20
<212> TYPE: DNA
<213> ORGANISM: Murine

<400> SEQUENCE: 3
atcactgcca cccagaagac                                                    20

<210> SEQ ID NO 4
<211> LENGTH: 20
<212> TYPE: DNA
<213> ORGANISM: Murine

<400> SEQUENCE: 4
```
cacattgggg gtaggaacac                                                  20

<210> SEQ ID NO 5
<211> LENGTH: 20
<212> TYPE: DNA
<213> ORGANISM: Murine

<400> SEQUENCE: 5
tcgtagcaaa ccaccaagtg                                                  20

<210> SEQ ID NO 6
<211> LENGTH: 20
<212> TYPE: DNA
<213> ORGANISM: Murine

<400> SEQUENCE: 6
agatagcaaa tcggctgacg                                                  20

<210> SEQ ID NO 7
<211> LENGTH: 22
<212> TYPE: DNA
<213> ORGANISM: Murine

<400> SEQUENCE: 7
agacaaagcc agagtccttc ag                                               22

<210> SEQ ID NO 8
<211> LENGTH: 21
<212> TYPE: DNA
<213> ORGANISM: Murine

<400> SEQUENCE: 8
taggagagca ttggaaattg g                                                21

<210> SEQ ID NO 9
<211> LENGTH: 20
<212> TYPE: DNA
<213> ORGANISM: Murine

<400> SEQUENCE: 9
cccactcacc tgctgctact                                                  20

<210> SEQ ID NO 10
<211> LENGTH: 20
<212> TYPE: DNA
<213> ORGANISM: Murine

<400> SEQUENCE: 10
tctggaccca ttccttcttg                                                  20

<210> SEQ ID NO 11
<211> LENGTH: 22
<212> TYPE: DNA
<213> ORGANISM: Murine

<400> SEQUENCE: 11
ctccaagcca aagtccttag ag                                               22

<210> SEQ ID NO 12
<211> LENGTH: 22
<212> TYPE: DNA
<213> ORGANISM: Murine

<400> SEQUENCE: 12

```
aggagctgtc attagggaca tc                                          22

<210> SEQ ID NO 13
<211> LENGTH: 20
<212> TYPE: DNA
<213> ORGANISM: Murine

<400> SEQUENCE: 13
gggcatacct ttatcctgag                                             20

<210> SEQ ID NO 14
<211> LENGTH: 20
<212> TYPE: DNA
<213> ORGANISM: Murine

<400> SEQUENCE: 14
ccactgaagt catccatgtc                                             20

<210> SEQ ID NO 15
<211> LENGTH: 23
<212> TYPE: DNA
<213> ORGANISM: Murine

<400> SEQUENCE: 15
ggcaggatct tggcaaccta gta                                         23

<210> SEQ ID NO 16
<211> LENGTH: 22
<212> TYPE: DNA
<213> ORGANISM: Murine

<400> SEQUENCE: 16
gtttggatcg gcacacaaag tc                                          22

<210> SEQ ID NO 17
<211> LENGTH: 20
<212> TYPE: DNA
<213> ORGANISM: Murine

<400> SEQUENCE: 17
agctccaaga ccaaggtgtc                                             20

<210> SEQ ID NO 18
<211> LENGTH: 20
<212> TYPE: DNA
<213> ORGANISM: Murine

<400> SEQUENCE: 18
cgaggttttc caaggagttg                                             20
```